US011224453B2

(12) United States Patent
Huffmaster et al.

(10) Patent No.: US 11,224,453 B2
(45) Date of Patent: Jan. 18, 2022

(54) APPARATUS AND METHODS FOR DISRUPTING INTERVERTEBRAL DISC TISSUE

(71) Applicant: Spinal Elements, Inc., Carlsbad, CA (US)

(72) Inventors: Andrew Huffmaster, Newark, CA (US); Jeffrey L. Emery, Emerald Hills, CA (US); Ricardo J. Simmons, Carlsbad, CA (US); Douglas M. Lorang, San Jose, CA (US); Jeffrey A. Doelling, Sunnyvale, CA (US); Russell Borg, Campbell, CA (US); Laurent B. Schaller, Los Altos, CA (US); Ebrahim M. Quddus, Fremont, CA (US); Sandeep Kunwar, Woodside, CA (US); James K. Lee, Castro Valley, CA (US); Timothy J. McGrath, Fremont, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 218 days.

(21) Appl. No.: 16/366,523

(22) Filed: Mar. 27, 2019

(65) Prior Publication Data
US 2019/0216482 A1    Jul. 18, 2019

Related U.S. Application Data

(62) Division of application No. 14/792,956, filed on Jul. 7, 2015, now Pat. No. 10,314,605.
(Continued)

(51) Int. Cl.
*A61B 17/32* (2006.01)
*A61B 17/295* (2006.01)
(Continued)

(52) U.S. Cl.
CPC .... *A61B 17/295* (2013.01); *A61B 17/320016* (2013.01); *A61B 2017/00261* (2013.01);
(Continued)

(58) Field of Classification Search
CPC ......... A61B 2017/00261; A61B 2017/320048; A61B 2017/32006; A61B 17/320016; A61B 17/295
See application file for complete search history.

(56) References Cited

U.S. PATENT DOCUMENTS 2,002,021 A    5/1935   Rouse
3,807,390 A    4/1974   Ostrowski et al.
(Continued)

FOREIGN PATENT DOCUMENTS

DE    4222121 C1    9/1993
DE    197 10 392    7/1999
(Continued)

OTHER PUBLICATIONS

Official Communication in European Application No. 08730402.8, dated Feb. 18, 2013.
(Continued)

*Primary Examiner* — Olivia C Chang
(74) *Attorney, Agent, or Firm* — Knobbe, Martens, Olson & Bear, LLP

(57) ABSTRACT

An apparatus for disrupting tissue in the intervertebral disc space that includes a barrier member having a first configuration for insertion into the disc space and a second configuration when deployed within the disc space. The second configuration of the barrier member is adapted to at least partially define a perimeter of a working region within the disc space. The apparatus also includes a tissue disruption tool configured for insertion into the working region.

30 Claims, 21 Drawing Sheets

Related U.S. Application Data

(60) Provisional application No. 62/021,960, filed on Jul. 8, 2014.

(51) Int. Cl.
*A61B 17/00* (2006.01)
*A61B 17/29* (2006.01)
*A61B 90/00* (2016.01)

(52) U.S. Cl.
CPC ............ *A61B 2017/2926* (2013.01); *A61B 2017/2927* (2013.01); *A61B 2017/2939* (2013.01); *A61B 2017/320004* (2013.01); *A61B 2017/32006* (2013.01); *A61B 2017/320008* (2013.01); *A61B 2017/320012* (2013.01); *A61B 2090/08021* (2016.02)

(56) References Cited

U.S. PATENT DOCUMENTS

| | | |
|---|---|---|
| 4,846,175 A | 7/1989 | Frimberger |
| 4,862,891 A | 9/1989 | Smith |
| 4,863,476 A | 9/1989 | Shepperd |
| 4,898,161 A | 2/1990 | Grundei |
| 5,129,889 A | 7/1992 | Hahn et al. |
| 5,192,327 A | 3/1993 | Brantigan |
| 5,201,742 A | 4/1993 | Hasson |
| 5,219,358 A | 6/1993 | Bendel et al. |
| 5,267,994 A | 12/1993 | Gentelia et al. |
| 5,306,310 A | 4/1994 | Siebels |
| 5,342,394 A | 8/1994 | Matsuno et al. |
| 5,345,945 A | 9/1994 | Hodgson et al. |
| 5,366,490 A | 11/1994 | Edwards et al. |
| 5,374,267 A | 12/1994 | Siegal |
| 5,383,884 A | 1/1995 | Summers |
| 5,397,304 A | 3/1995 | Truckai |
| 5,397,364 A | 3/1995 | Kozak et al. |
| 5,423,806 A | 6/1995 | Dale et al. |
| 5,433,739 A | 7/1995 | Sluijter et al. |
| 5,445,639 A | 8/1995 | Kuslich et al. |
| 5,470,043 A | 11/1995 | Marts et al. |
| 5,487,757 A | 1/1996 | Truckai et al. |
| 5,500,012 A | 3/1996 | Brucker et al. |
| 5,540,696 A | 7/1996 | Booth, Jr. et al. |
| 5,549,679 A | 8/1996 | Kuslich |
| 5,554,163 A | 9/1996 | Shturman |
| 5,571,147 A | 11/1996 | Sluijter et al. |
| 5,571,189 A | 11/1996 | Kuslich |
| 5,599,346 A | 2/1997 | Edwards et al. |
| 5,697,909 A | 12/1997 | Eggers et al. |
| 5,716,416 A | 2/1998 | Lin |
| 5,718,707 A | 2/1998 | Mikhail |
| 5,755,661 A | 5/1998 | Schwartzman |
| 5,755,732 A | 5/1998 | Green et al. |
| 5,755,797 A | 5/1998 | Baumgartner |
| 5,788,713 A | 8/1998 | Dubach et al. |
| 5,851,214 A | 12/1998 | Larsen et al. |
| 5,871,501 A | 2/1999 | Leschinsky et al. |
| 5,885,217 A | 3/1999 | Gisselberg et al. |
| 5,916,166 A | 6/1999 | Reiss et al. |
| 5,919,235 A | 7/1999 | Husson et al. |
| 5,980,471 A | 11/1999 | Jafari |
| 5,980,504 A | 11/1999 | Sharkey et al. |
| 6,007,570 A | 12/1999 | Sharkey et al. |
| 6,019,765 A | 2/2000 | Thornhill et al. |
| 6,039,761 A | 3/2000 | Li et al. |
| 6,059,829 A | 5/2000 | Schläpfer et al. |
| 6,099,514 A | 8/2000 | Sharkey et al. |
| 6,126,660 A | 10/2000 | Dietz |
| 6,126,682 A | 10/2000 | Sharkey et al. |
| 6,183,517 B1 | 2/2001 | Suddaby |
| 6,224,630 B1 | 5/2001 | Bao et al. |
| 6,228,022 B1 | 5/2001 | Friesem et al. |
| 6,245,072 B1 | 6/2001 | Zdeblick |
| 6,245,107 B1 | 6/2001 | Ferree |
| 6,277,112 B1 | 8/2001 | Underwood et al. |
| 6,332,895 B1 | 12/2001 | Suddaby |
| 6,375,635 B1 | 4/2002 | Moutafis et al. |
| 6,387,130 B1 | 5/2002 | Stone et al. |
| 6,419,704 B1 | 7/2002 | Ferree |
| 6,436,142 B1 | 8/2002 | Paes et al. |
| 6,454,806 B1 | 9/2002 | Cohen et al. |
| 6,468,270 B1 | 10/2002 | Hovda et al. |
| 6,488,710 B2 | 12/2002 | Besselink |
| 6,491,690 B1 | 12/2002 | Goble et al. |
| 6,500,205 B1 | 12/2002 | Michelson |
| 6,530,926 B1 | 3/2003 | Davison |
| 6,551,319 B2 | 4/2003 | Lieberman |
| 6,554,833 B2 | 4/2003 | Levy et al. |
| 6,558,383 B2 | 5/2003 | Cunningham et al. |
| 6,558,386 B2 | 5/2003 | Cragg |
| 6,558,390 B2 | 5/2003 | Cragg |
| 6,562,033 B2 | 5/2003 | Shah et al. |
| 6,592,625 B2 | 7/2003 | Cauthen |
| 6,595,998 B2 | 7/2003 | Johnson et al. |
| 6,602,248 B1 | 8/2003 | Sharps et al. |
| 6,607,505 B1 | 8/2003 | Thompson et al. |
| 6,607,530 B1 | 8/2003 | Carl et al. |
| 6,670,505 B1 | 8/2003 | Thompson et al. |
| 6,620,196 B1 | 9/2003 | Trieu |
| 6,656,178 B1 | 12/2003 | Veldhuizen et al. |
| 6,676,665 B2 | 1/2004 | Foley et al. |
| 6,714,822 B2 | 3/2004 | King et al. |
| 6,726,684 B1 | 4/2004 | Woloszko et al. |
| 6,733,496 B2 | 5/2004 | Sharkey et al. |
| 6,749,605 B2 | 6/2004 | Ashley et al. |
| 6,764,491 B2 | 7/2004 | Frey et al. |
| 6,767,347 B2 | 7/2004 | Sharkey et al. |
| 6,773,432 B1 | 8/2004 | Clayman et al. |
| 6,821,276 B2 | 11/2004 | Lambrecht et al. |
| 6,830,570 B1 | 12/2004 | Frey et al. |
| 6,878,155 B2 | 4/2005 | Sharkey et al. |
| 6,923,811 B1 | 8/2005 | Carl et al. |
| 6,939,351 B2 | 9/2005 | Eckman |
| 6,953,458 B2 | 10/2005 | Loeb |
| 6,964,667 B2 | 11/2005 | Shaolian et al. |
| 6,976,949 B2 | 12/2005 | Winkler et al. |
| 7,004,970 B2 | 2/2006 | Cauthen, III et al. |
| 7,008,432 B2 | 3/2006 | Schlapfer et al. |
| 7,025,765 B2 | 4/2006 | Balbierz et al. |
| 7,052,516 B2 | 5/2006 | Cauthen, III et al. |
| 7,056,321 B2 | 6/2006 | Pagliuca et al. |
| 7,069,087 B2 | 6/2006 | Sharkey et al. |
| 7,087,055 B2 | 8/2006 | Lim et al. |
| 7,087,058 B2 | 8/2006 | Cragg |
| 7,114,501 B2 | 10/2006 | Johnson et al. |
| 7,124,761 B2 | 10/2006 | Lambrecht et al. |
| 7,144,397 B2 | 12/2006 | Lambrecht et al. |
| 7,179,225 B2 | 2/2007 | Shluzas et al. |
| 7,204,853 B2 | 4/2007 | Gordon et al. |
| 7,211,055 B2 | 5/2007 | Diederich et al. |
| 7,241,297 B2 | 7/2007 | Shaolian et al. |
| 7,252,686 B2 | 8/2007 | Carrison et al. |
| 7,267,687 B2 | 9/2007 | McGuckin, Jr. |
| 7,282,020 B2 | 10/2007 | Kaplan |
| 7,309,336 B2 | 12/2007 | Ashley et al. |
| 7,318,823 B2 | 1/2008 | Sharps et al. |
| 7,318,826 B2 | 1/2008 | Teitelbaum et al. |
| 7,322,962 B2 | 1/2008 | Forrest |
| 7,331,956 B2 | 2/2008 | Hovda et al. |
| 7,331,963 B2 | 2/2008 | Bryan et al. |
| RE40,156 E | 3/2008 | Sharps et al. |
| 7,618,458 B2 | 11/2009 | Biedermann et al. |
| 7,682,378 B2 | 3/2010 | Truckai et al. |
| 7,753,912 B2 | 7/2010 | Raymond et al. |
| 7,758,647 B2 | 7/2010 | Arnin et al. |
| 7,771,432 B2 | 8/2010 | Schwab et al. |
| 7,776,051 B2 | 8/2010 | Colleran et al. |
| 7,824,445 B2 | 11/2010 | Biro et al. |
| 7,887,568 B2 | 2/2011 | Ahlgren |
| 7,901,460 B2 | 3/2011 | Sherman |
| 7,922,767 B2 | 4/2011 | Sack et al. |
| 7,947,078 B2 | 5/2011 | Siegal |
| 7,963,915 B2 | 6/2011 | Bleich |

(56) References Cited

U.S. PATENT DOCUMENTS

| | | |
|---|---|---|
| 8,021,429 B2 | 9/2011 | Viker |
| 8,025,697 B2 | 9/2011 | McClellan, III et al. |
| 8,083,796 B1 | 12/2011 | Raiszadeh et al. |
| 8,123,750 B2 | 2/2012 | Norton et al. |
| 8,128,662 B2 | 3/2012 | Altarac et al. |
| 8,137,401 B2 | 3/2012 | Stad et al. |
| 8,142,507 B2 | 3/2012 | McGuckin, Jr. |
| 8,246,622 B2 | 8/2012 | Siegal et al. |
| 8,252,001 B2 | 8/2012 | Quimo et al. |
| 8,252,054 B2 | 8/2012 | Greenhalgh et al. |
| 8,377,070 B2 | 2/2013 | Gauthier |
| 8,394,102 B2 | 3/2013 | Garabedian et al. |
| 8,454,617 B2 | 6/2013 | Schaller et al. |
| 8,454,622 B2 | 6/2013 | Blain et al. |
| 8,470,043 B2 | 6/2013 | Schaller et al. |
| 8,579,980 B2 | 11/2013 | DeLurio et al. |
| 8,628,577 B1 | 1/2014 | Jimenez |
| 8,632,591 B2 | 1/2014 | Vila et al. |
| 8,663,332 B1 | 3/2014 | To et al. |
| 8,685,031 B2 | 4/2014 | Kleiner et al. |
| 8,764,806 B2 | 7/2014 | Abdou |
| 8,906,028 B2 | 12/2014 | Kleiner |
| 8,968,408 B2 | 3/2015 | Schaller et al. |
| 8,974,464 B2 | 3/2015 | Johnson et al. |
| 8,979,860 B2 | 3/2015 | Voellmicke et al. |
| 8,986,385 B2 | 3/2015 | Hall |
| 9,034,041 B2 | 5/2015 | Wolters et al. |
| 9,039,771 B2 | 5/2015 | Glerum et al. |
| 9,161,773 B2 | 10/2015 | Schaller et al. |
| 9,308,022 B2 | 4/2016 | Chitre et al. |
| 9,351,851 B2 | 5/2016 | Huffmaster et al. |
| 9,480,574 B2 | 11/2016 | Lee et al. |
| 9,566,170 B2 | 2/2017 | Schell et al. |
| 9,642,712 B2 | 5/2017 | Schaller et al. |
| 9,827,031 B2 | 11/2017 | Emery et al. |
| 9,955,961 B2 | 5/2018 | Huffmaster et al. |
| 10,022,243 B2 | 7/2018 | Emery et al. |
| 10,231,843 B2 | 3/2019 | Lee et al. |
| 10,258,228 B2 | 4/2019 | Genovese et al. |
| 10,285,821 B2 | 5/2019 | Schaller et al. |
| 10,314,605 B2 | 6/2019 | Huffmaster et al. |
| 10,426,629 B2 | 10/2019 | Schaller et al. |
| 10,575,963 B2 | 3/2020 | Schaller et al. |
| 10,709,577 B2 | 7/2020 | Lorang et al. |
| 10,758,286 B2 | 9/2020 | Ammerman et al. |
| 2001/0023348 A1 | 9/2001 | Ashley et al. |
| 2001/0029377 A1 | 10/2001 | Aebi et al. |
| 2001/0031981 A1 | 10/2001 | Evans et al. |
| 2002/0019637 A1 | 2/2002 | Frey et al. |
| 2002/0026197 A1 | 2/2002 | Foley et al. |
| 2002/0128716 A1 | 9/2002 | Cohen et al. |
| 2002/0147444 A1 | 10/2002 | Shah et al. |
| 2002/0156530 A1 | 10/2002 | Lambrecht et al. |
| 2003/0009223 A1 | 1/2003 | Fehling et al. |
| 2003/0014047 A1 | 1/2003 | Woloszko et al. |
| 2003/0040796 A1 | 2/2003 | Ferree |
| 2003/0065358 A1 | 4/2003 | Frecker et al. |
| 2003/0083747 A1 | 5/2003 | Winterbottom et al. |
| 2003/0158545 A1 | 8/2003 | Hovda et al. |
| 2003/0158553 A1 | 8/2003 | Michelson |
| 2003/0187453 A1 | 10/2003 | Schlapfer et al. |
| 2003/0204189 A1 | 10/2003 | Cragg |
| 2003/0220650 A1 | 11/2003 | Major et al. |
| 2004/0002762 A1 | 1/2004 | Hawkins |
| 2004/0015218 A1 | 1/2004 | Finch et al. |
| 2004/0024463 A1 | 2/2004 | Thomas, Jr. et al. |
| 2004/0049180 A1 | 3/2004 | Sharps et al. |
| 2004/0059333 A1 | 3/2004 | Carl et al. |
| 2004/0064144 A1 | 4/2004 | Johnson et al. |
| 2004/0073216 A1 | 4/2004 | Lieberman |
| 2004/0087994 A1 | 5/2004 | Suddaby |
| 2004/0092988 A1 | 5/2004 | Shaolian et al. |
| 2004/0102774 A1 | 5/2004 | Trieu |
| 2004/0106940 A1 | 6/2004 | Shaolian et al. |
| 2004/0116922 A1 | 6/2004 | Hovda et al. |
| 2004/0127893 A1 | 7/2004 | Hovda |
| 2004/0148028 A1 | 7/2004 | Ferree et al. |
| 2004/0153064 A1 | 8/2004 | Foley et al. |
| 2004/0167625 A1 | 8/2004 | Beyar et al. |
| 2004/0193158 A1 | 9/2004 | Lim et al. |
| 2004/0230198 A1 | 11/2004 | Manzi et al. |
| 2004/0230309 A1 | 11/2004 | DiMauro et al. |
| 2004/0249464 A1 | 12/2004 | Bindseil et al. |
| 2004/0260305 A1 | 12/2004 | Gorensek et al. |
| 2005/0021030 A1 | 1/2005 | Pagliuca et al. |
| 2005/0021041 A1 | 1/2005 | Michelson |
| 2005/0033292 A1 | 2/2005 | Teitelbaum et al. |
| 2005/0038517 A1 | 2/2005 | Carrison et al. |
| 2005/0049623 A1 | 3/2005 | Moore et al. |
| 2005/0065610 A1 | 3/2005 | Pisharodi |
| 2005/0070911 A1 | 3/2005 | Carrison et al. |
| 2005/0080425 A1 | 4/2005 | Bhatnagar et al. |
| 2005/0090833 A1 | 4/2005 | DiPoto |
| 2005/0090899 A1 | 4/2005 | DiPoto |
| 2005/0107878 A1 | 5/2005 | Conchy |
| 2005/0113832 A1 | 5/2005 | Molz, IV et al. |
| 2005/0119750 A1 | 6/2005 | Studer |
| 2005/0131540 A1 | 6/2005 | Trieu |
| 2005/0131541 A1 | 6/2005 | Trieu |
| 2005/0137601 A1 | 6/2005 | Assell et al. |
| 2005/0137605 A1 | 6/2005 | Assell et al. |
| 2005/0149049 A1 | 7/2005 | Assell et al. |
| 2005/0182414 A1 | 8/2005 | Manzi et al. |
| 2005/0182416 A1 | 8/2005 | Lim et al. |
| 2005/0187537 A1 | 8/2005 | Loeb et al. |
| 2005/0203527 A1 | 9/2005 | Carrison et al. |
| 2005/0228391 A1 | 10/2005 | Levy et al. |
| 2005/0234493 A1 | 10/2005 | Carr et al. |
| 2005/0240171 A1 | 10/2005 | Forrest |
| 2005/0251134 A1 | 11/2005 | Woloszko et al. |
| 2005/0251177 A1 | 11/2005 | Saadat et al. |
| 2005/0256525 A1 | 11/2005 | Culbert et al. |
| 2005/0261683 A1 | 11/2005 | Veldhuizen et al. |
| 2005/0261684 A1 | 11/2005 | Shaolian et al. |
| 2005/0261692 A1 | 11/2005 | Carrison et al. |
| 2005/0273173 A1 | 12/2005 | Gordon et al. |
| 2005/0278027 A1 | 12/2005 | Hyde |
| 2006/0015131 A1 | 1/2006 | Kierce et al. |
| 2006/0025797 A1 | 2/2006 | Lock et al. |
| 2006/0030933 A1 | 2/2006 | DeLegge et al. |
| 2006/0036241 A1 | 2/2006 | Siegal |
| 2006/0041258 A1 | 2/2006 | Galea |
| 2006/0041295 A1 | 2/2006 | Osypka |
| 2006/0047178 A1 | 3/2006 | Winkler et al. |
| 2006/0052793 A1 | 3/2006 | Heinz |
| 2006/0058826 A1 | 3/2006 | Evans et al. |
| 2006/0058876 A1 | 3/2006 | McKinley |
| 2006/0074425 A1 | 4/2006 | Sutterlin et al. |
| 2006/0089646 A1 | 4/2006 | Bonutti |
| 2006/0116689 A1 | 6/2006 | Albans |
| 2006/0129244 A1 | 6/2006 | Ensign et al. |
| 2006/0136064 A1 | 6/2006 | Sherman |
| 2006/0149268 A1 | 7/2006 | Truckai et al. |
| 2006/0161162 A1 | 7/2006 | Lambrecht et al. |
| 2006/0178666 A1 | 8/2006 | Cosman et al. |
| 2006/0189999 A1 | 8/2006 | Zwirkoski |
| 2006/0195091 A1 | 8/2006 | McGraw et al. |
| 2006/0195094 A1 | 8/2006 | McGraw et al. |
| 2006/0206116 A1 | 9/2006 | Yeung |
| 2006/0217811 A1 | 9/2006 | Lambrecht et al. |
| 2006/0224154 A1 | 10/2006 | Shadduck et al. |
| 2006/0224241 A1 | 10/2006 | Butler et al. |
| 2006/0229625 A1 | 10/2006 | Truckai et al. |
| 2006/0235418 A1 | 10/2006 | Gil et al. |
| 2006/0241577 A1 | 10/2006 | Balbierz et al. |
| 2006/0247600 A1 | 11/2006 | Yeung et al. |
| 2006/0247784 A1 | 11/2006 | Kim |
| 2006/0265076 A1 | 11/2006 | Carter et al. |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0010848 A1 | 1/2007 | Leung et al. |
| 2007/0016273 A1 | 1/2007 | Scarborough et al. |

(56) References Cited

U.S. PATENT DOCUMENTS

| | | |
|---|---|---|
| 2007/0027545 A1 | 2/2007 | Carls et al. |
| 2007/0050030 A1 | 3/2007 | Kim |
| 2007/0055259 A1 | 3/2007 | Norton et al. |
| 2007/0055262 A1 | 3/2007 | Tomita et al. |
| 2007/0060935 A1 | 3/2007 | Schwardt et al. |
| 2007/0067035 A1 | 3/2007 | Falahee |
| 2007/0093822 A1 | 4/2007 | Dutoit et al. |
| 2007/0093899 A1 | 4/2007 | Dutoit et al. |
| 2007/0118219 A1 | 5/2007 | Hyde |
| 2007/0123888 A1 | 5/2007 | Bleich et al. |
| 2007/0123903 A1 | 5/2007 | Raymond et al. |
| 2007/0123986 A1 | 5/2007 | Schaller |
| 2007/0149978 A1 | 6/2007 | Shezifi et al. |
| 2007/0149990 A1 | 6/2007 | Palmer et al. |
| 2007/0162032 A1 | 7/2007 | Johnson et al. |
| 2007/0162062 A1 | 7/2007 | Norton et al. |
| 2007/0162127 A1 | 7/2007 | Peterman et al. |
| 2007/0162135 A1 | 7/2007 | Segal et al. |
| 2007/0168041 A1 | 7/2007 | Kadiyala |
| 2007/0168043 A1 | 7/2007 | Ferree |
| 2007/0173939 A1 | 7/2007 | Kim et al. |
| 2007/0175959 A1 | 8/2007 | Shelton, IV et al. |
| 2007/0198021 A1 | 8/2007 | Wales |
| 2007/0198025 A1 | 8/2007 | Trieu et al. |
| 2007/0208426 A1 | 9/2007 | Trieu |
| 2007/0213704 A1 | 9/2007 | Truckai et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0225703 A1 | 9/2007 | Schmitz et al. |
| 2007/0233143 A1 | 10/2007 | Josse et al. |
| 2007/0255286 A1 | 11/2007 | Trieu |
| 2007/0255406 A1 | 11/2007 | Trieu |
| 2007/0255703 A1 | 11/2007 | Maryuyama et al. |
| 2007/0260252 A1 | 11/2007 | Schmitz et al. |
| 2007/0260270 A1 | 11/2007 | Assell et al. |
| 2007/0260315 A1 | 11/2007 | Foley et al. |
| 2007/0265652 A1 | 11/2007 | Assell et al. |
| 2007/0265691 A1 | 11/2007 | Swanson |
| 2007/0276406 A1 | 11/2007 | Mahoney et al. |
| 2007/0299521 A1 | 12/2007 | Glenn et al. |
| 2008/0009826 A1 | 1/2008 | Miller et al. |
| 2008/0009828 A1 | 1/2008 | Miller et al. |
| 2008/0009847 A1 | 1/2008 | Ricart et al. |
| 2008/0009875 A1 | 1/2008 | Sankaran et al. |
| 2008/0009876 A1 | 1/2008 | Sankaran et al. |
| 2008/0009877 A1 | 1/2008 | Sankaran et al. |
| 2008/0015639 A1 | 1/2008 | Bjork et al. |
| 2008/0021435 A1 | 1/2008 | Miller et al. |
| 2008/0027407 A1 | 1/2008 | Miller et al. |
| 2008/0033465 A1 | 2/2008 | Schmitz et al. |
| 2008/0058707 A1 | 3/2008 | Ashley et al. |
| 2008/0065080 A1 | 3/2008 | Assell et al. |
| 2008/0065092 A1 | 3/2008 | Assell et al. |
| 2008/0065093 A1 | 3/2008 | Assell et al. |
| 2008/0065094 A1 | 3/2008 | Assell et al. |
| 2008/0086157 A1 | 4/2008 | Stad et al. |
| 2008/0114367 A1 | 5/2008 | Meyer |
| 2008/0147113 A1 | 6/2008 | Nobis et al. |
| 2008/0161809 A1 | 7/2008 | Schmitz et al. |
| 2008/0177259 A1 | 7/2008 | Wu |
| 2008/0183204 A1 | 7/2008 | Greenhalgh et al. |
| 2008/0221687 A1 | 9/2008 | Viker |
| 2008/0228135 A1 | 9/2008 | Snoderly |
| 2008/0249628 A1 | 10/2008 | Altarac et al. |
| 2008/0287995 A1 | 11/2008 | Gauthier |
| 2008/0294171 A1 | 11/2008 | Boehm, Jr. et al. |
| 2008/0300636 A1 | 12/2008 | Carli et al. |
| 2009/0012612 A1 | 1/2009 | White et al. |
| 2009/0024217 A1 | 1/2009 | Levy et al. |
| 2009/0105711 A1 | 4/2009 | Mitchell et al. |
| 2009/0143716 A1 | 6/2009 | Lowry et al. |
| 2009/0157187 A1 | 6/2009 | Richelsoph |
| 2009/0198241 A1 | 8/2009 | Phan |
| 2009/0198245 A1 | 8/2009 | Phan |
| 2009/0234454 A1 | 9/2009 | Siegal |
| 2010/0030216 A1 | 2/2010 | Arcenio |
| 2010/0114179 A1 | 5/2010 | Moore et al. |
| 2010/0131005 A1 | 5/2010 | Conlon |
| 2010/0179578 A1 | 7/2010 | Tannoury et al. |
| 2010/0185291 A1 | 7/2010 | Jimenez et al. |
| 2010/0198263 A1 | 8/2010 | Siegal et al. |
| 2010/0228091 A1 | 9/2010 | Widenhouse et al. |
| 2010/0262147 A1 | 10/2010 | Siegal et al. |
| 2010/0262242 A1* | 10/2010 | Chavatte ............ A61B 17/7097 623/17.12 |
| 2010/0286782 A1 | 11/2010 | Schaller et al. |
| 2010/0298864 A1 | 11/2010 | Castro |
| 2011/0015638 A1 | 1/2011 | Pischl et al. |
| 2011/0015747 A1 | 1/2011 | McManus et al. |
| 2011/0112455 A1 | 5/2011 | Rocklin |
| 2011/0125266 A1 | 5/2011 | Rodgers et al. |
| 2011/0144440 A1 | 6/2011 | Cropper et al. |
| 2011/0172722 A1 | 7/2011 | Verhulst et al. |
| 2011/0208306 A1 | 8/2011 | Farris |
| 2011/0245926 A1 | 10/2011 | Kitchen |
| 2011/0307063 A1 | 12/2011 | Schaller et al. |
| 2011/0313529 A1 | 12/2011 | Schaller et al. |
| 2012/0022651 A1 | 1/2012 | Akyuz et al. |
| 2012/0071977 A1 | 3/2012 | Oglaza et al. |
| 2012/0071980 A1 | 3/2012 | Purcell et al. |
| 2012/0089231 A1 | 4/2012 | Prestigiacomo |
| 2012/0123426 A1 | 5/2012 | Quimo |
| 2012/0136442 A1 | 5/2012 | Kleiner |
| 2012/0136448 A1 | 5/2012 | Seifert et al. |
| 2012/0150241 A1 | 6/2012 | Ragab et al. |
| 2012/0232664 A1 | 9/2012 | Ulrich et al. |
| 2012/0277861 A1 | 11/2012 | Steele et al. |
| 2012/0283748 A1 | 11/2012 | Ortiz et al. |
| 2013/0053863 A1 | 2/2013 | Juravic et al. |
| 2013/0110239 A1 | 5/2013 | Siegal et al. |
| 2013/0116791 A1 | 5/2013 | Theofilos |
| 2013/0144391 A1 | 6/2013 | Siegal et al. |
| 2013/0158667 A1 | 6/2013 | Tabor et al. |
| 2013/0204374 A1 | 8/2013 | Milella, Jr. |
| 2013/0282143 A1 | 10/2013 | Perkins et al. |
| 2013/0304070 A1 | 11/2013 | Nelson et al. |
| 2014/0058513 A1 | 2/2014 | Gahman et al. |
| 2014/0067073 A1 | 3/2014 | Hauck |
| 2014/0163326 A1 | 6/2014 | Forsell |
| 2014/0235949 A1 | 8/2014 | Smith |
| 2014/0236296 A1 | 8/2014 | Wagner et al. |
| 2014/0249629 A1 | 9/2014 | Moskowitz et al. |
| 2014/0257484 A1 | 9/2014 | Flower et al. |
| 2014/0316427 A1* | 10/2014 | Yoon .............. A61B 17/320783 606/114 |
| 2015/0012000 A1 | 1/2015 | Siegal et al. |
| 2015/0051701 A1 | 2/2015 | Glerum et al. |
| 2015/0100124 A1 | 4/2015 | Whipple |
| 2015/0112437 A1 | 4/2015 | Davis et al. |
| 2015/0112438 A1 | 4/2015 | McLean |
| 2015/0148908 A1 | 5/2015 | Marino et al. |
| 2016/0007979 A1 | 1/2016 | Bhagat et al. |
| 2016/0287409 A1 | 10/2016 | Ziemek |
| 2016/0367332 A1 | 12/2016 | Shah et al. |
| 2017/0135704 A1 | 5/2017 | Abbasi |
| 2019/0167440 A1 | 6/2019 | Lee et al. |
| 2019/0216612 A1 | 7/2019 | Schaller et al. |
| 2020/0345401 A1 | 11/2020 | McHale et al. |
| 2021/0113252 A1 | 4/2021 | Ammerman et al. |
| 2021/0154024 A1 | 5/2021 | Lorang et al. |
| 2021/0169459 A1 | 6/2021 | Pacheco-Serrant et al. |

FOREIGN PATENT DOCUMENTS

| | | |
|---|---|---|
| EP | 0682910 A1 | 11/1995 |
| EP | 1 157 676 | 11/2001 |
| FR | 2 900 814 | 11/2007 |
| JP | 2002-028171 | 1/2002 |
| WO | WO98/17190 A3 | 4/1998 |
| WO | WO 98/034552 | 8/1998 |
| WO | WO 99/021500 | 5/1999 |
| WO | WO 99/47058 | 9/1999 |
| WO | WO 00/074605 | 12/2000 |

(56) References Cited

FOREIGN PATENT DOCUMENTS

| WO | WO 03/024344 | 3/2003 |
|---|---|---|
| WO | WO 2005/048856 | 6/2005 |
| WO | WO 2006/047587 | 5/2006 |
| WO | WO 2006/072941 | 7/2006 |
| WO | WO 2007/100914 A2 | 9/2007 |
| WO | WO 2008/036505 | 3/2008 |
| WO | WO 2008/084479 | 7/2008 |
| WO | WO 2008/103832 | 8/2008 |
| WO | WO 2010/008353 | 1/2010 |
| WO | WO 2011/150350 | 12/2011 |
| WO | WO 2012/048187 | 4/2012 |
| WO | WO 2012/178018 | 12/2012 |
| WO | WO 2013/043850 | 3/2013 |
| WO | WO 2014/158680 | 10/2014 |
| WO | WO 2019/148083 | 8/2019 |
| WO | WO 2019/178575 | 9/2019 |

OTHER PUBLICATIONS

International Search Report and Written Opinion in International Application No. PCT/US2008/054590, dated Aug. 22, 2008.
International Preliminary Report on Patentability and Written Opinion in International Application No. PCT/US2008/054590, dated Aug. 28, 2009.
International Search Report and Written Opinion in International Application No. PCT/US2019/015386, dated May 23, 2019.
International Preliminary Report on Patentability and Written Opinion in International Application No. PCT/US2019/015386, dated Aug. 13, 2020.
International Search Report and Written Opinion in International Application No. PCT/US2019/022632, dated May 30, 2019.
International Preliminary Report on Patentability and Written Opinion in International Application No. PCT/US2019/022632, dated Oct. 1, 2020.
International Search Report and Written Opinion in International Application No. PCT/US2014/019246, dated Aug. 19, 2014.
International Preliminary Report on Patentability and Written Opinion in International Application No. PCT/US2014/019246, dated Sep. 24, 2015.
Office Communication for U.S. Appl. No. 13/804,847, dated Jul. 13, 2015.
Office Communication for U.S. Appl. No. 13/804,847, dated Oct. 16, 2015.
Extended European Search Report for European Patent Application No. 11787510.4, dated Oct. 15, 2013.
International Search Report and Written Opinion for PCT Patent Application No. PCT/US2011/038377, dated Aug. 25, 2011.
International Search Report and Written Opinion for PCT Patent Application No. PCT/US2013/068906, dated Feb. 6, 2014.

* cited by examiner

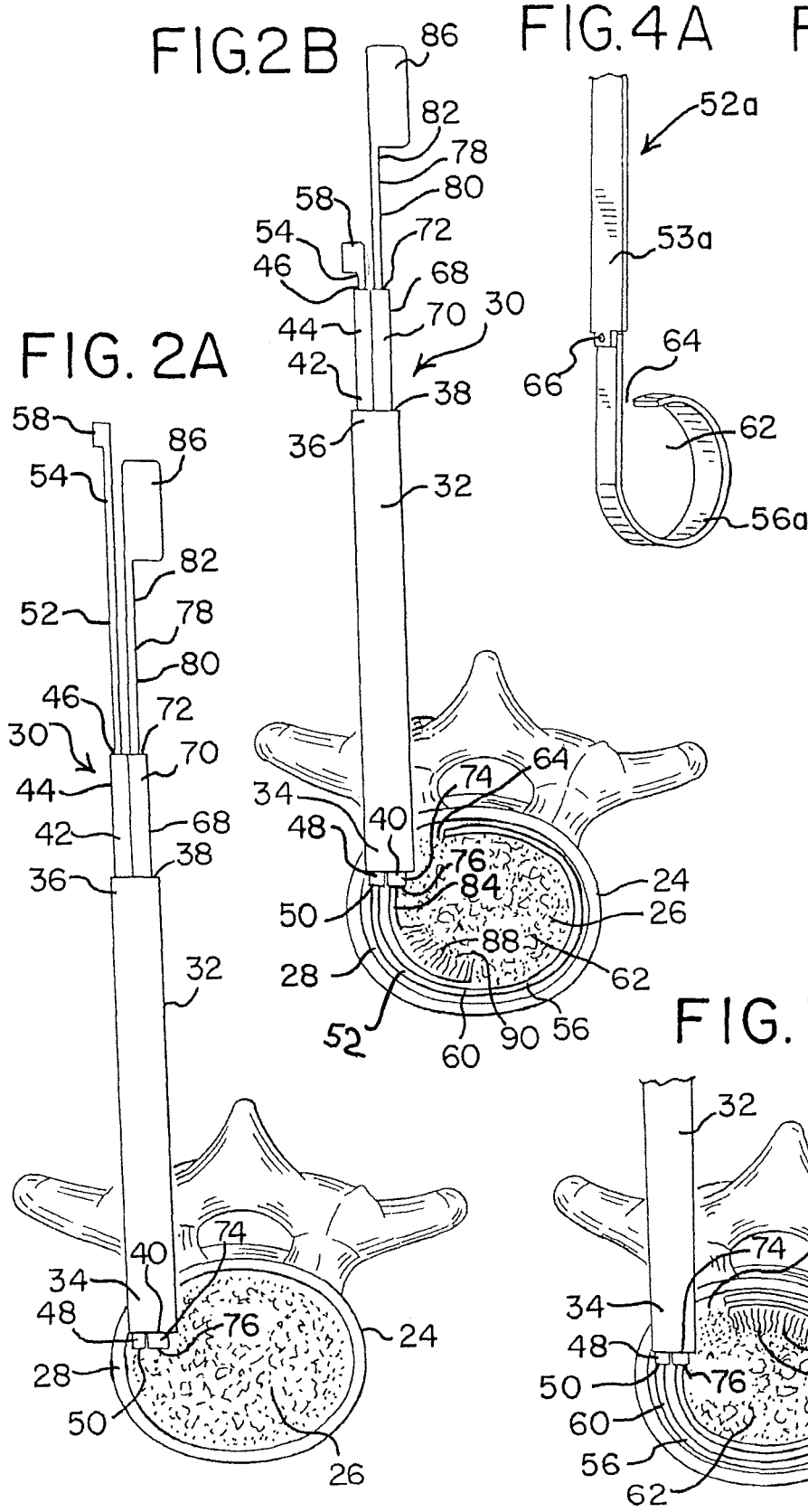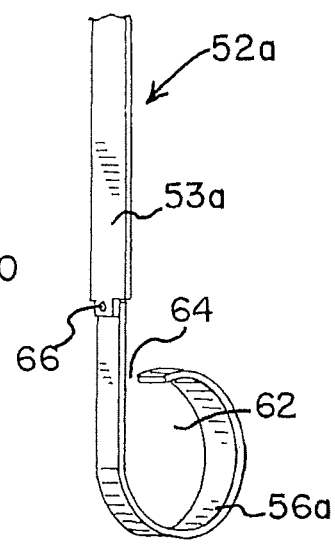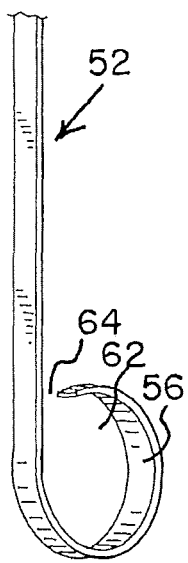

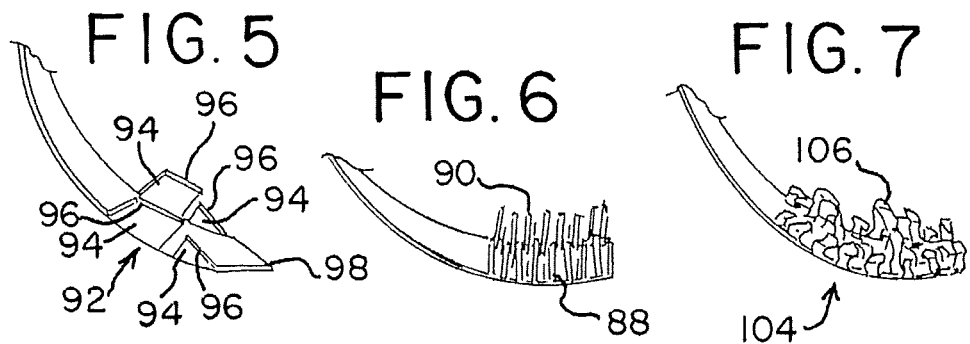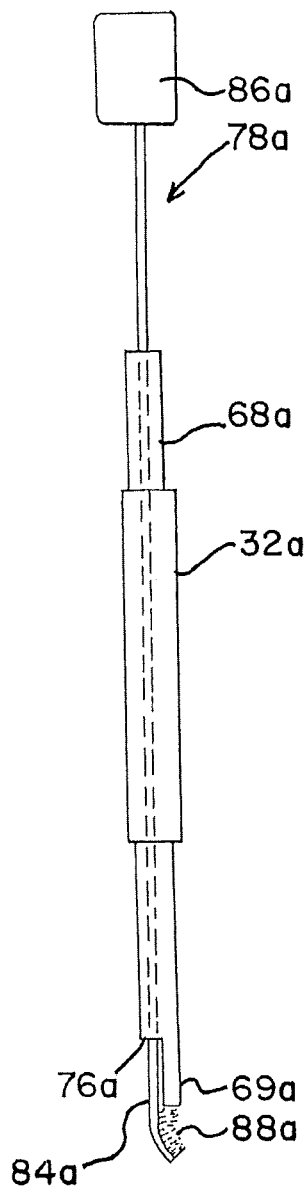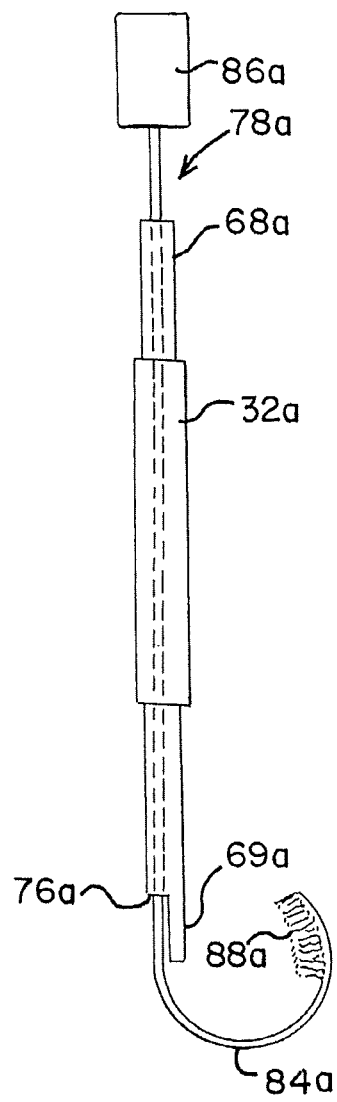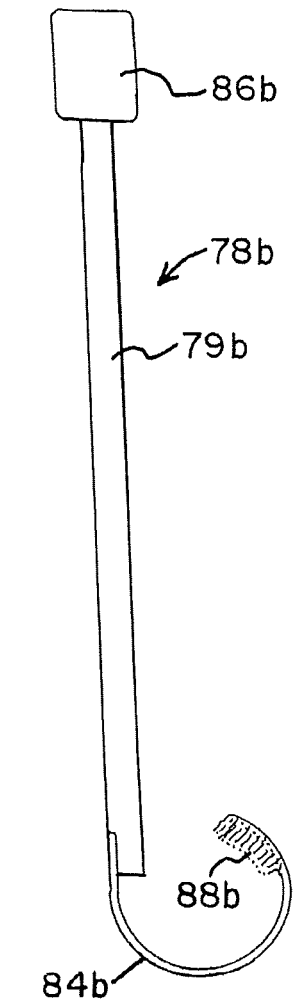

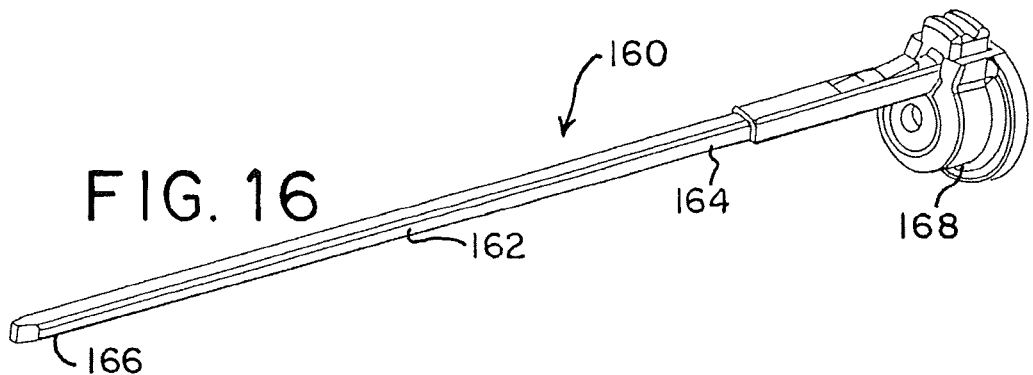
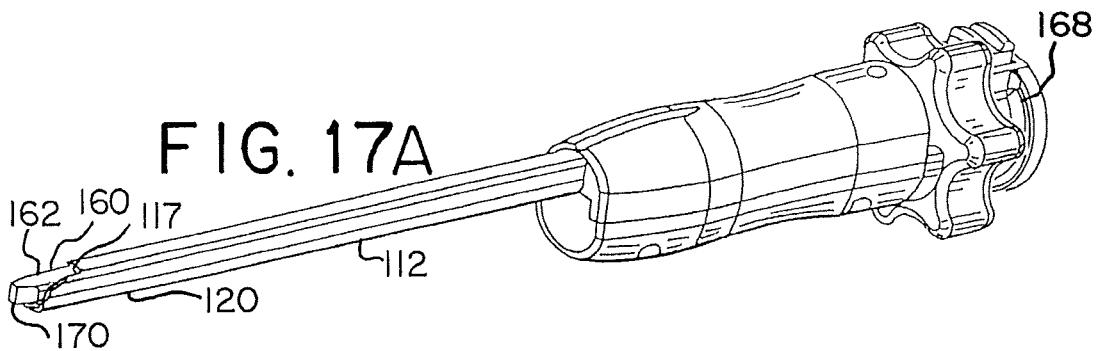
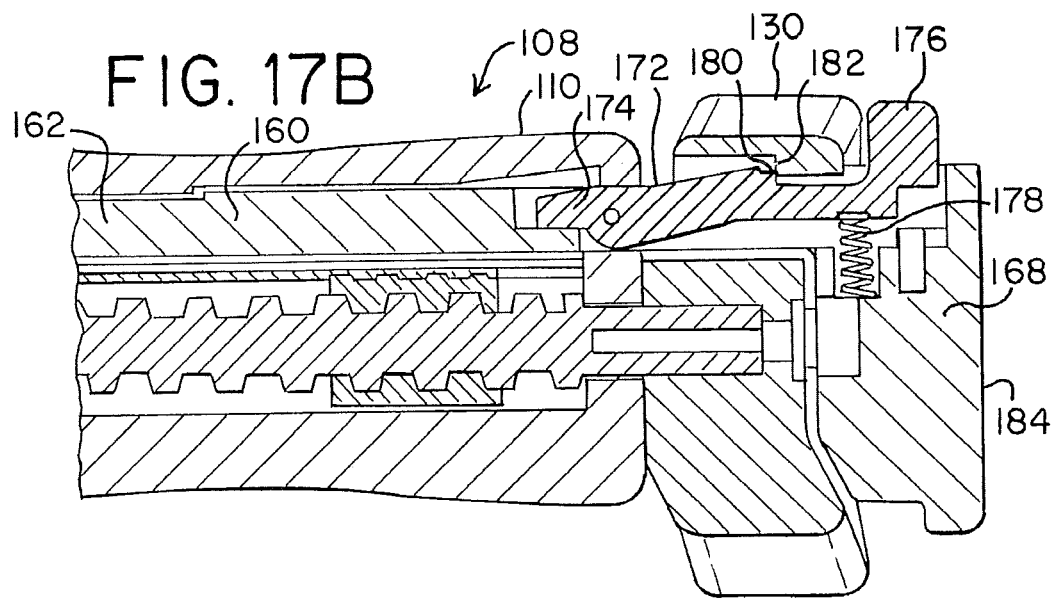

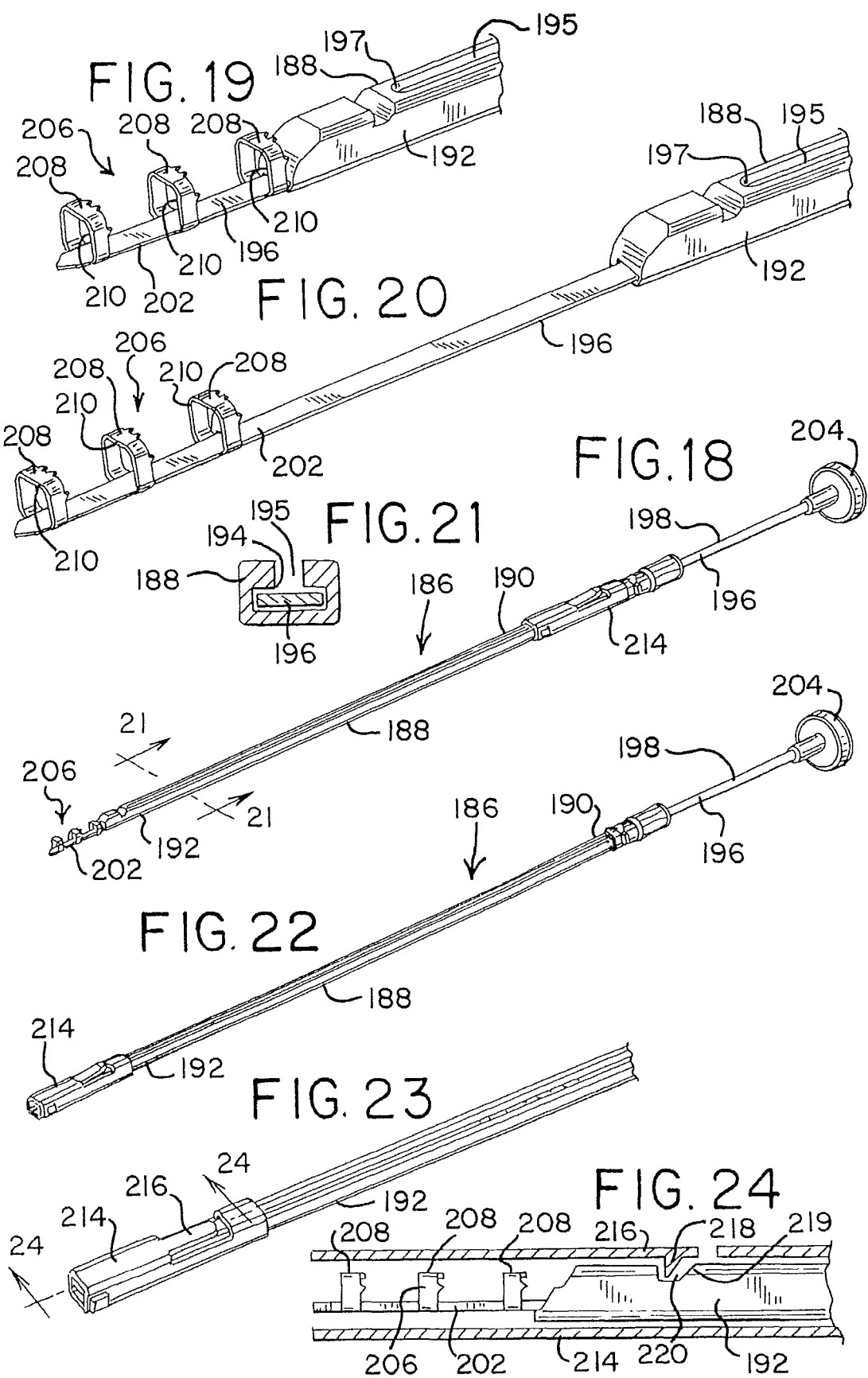

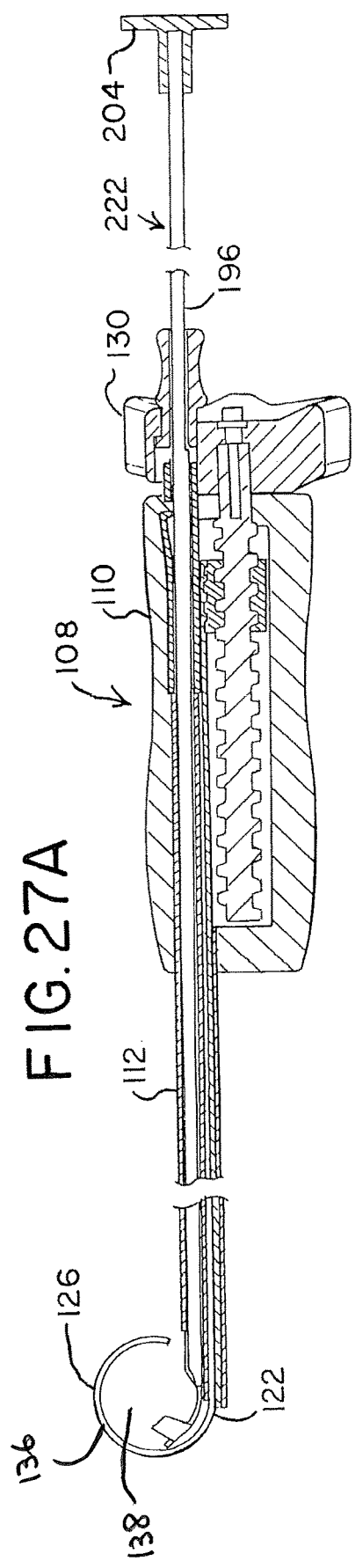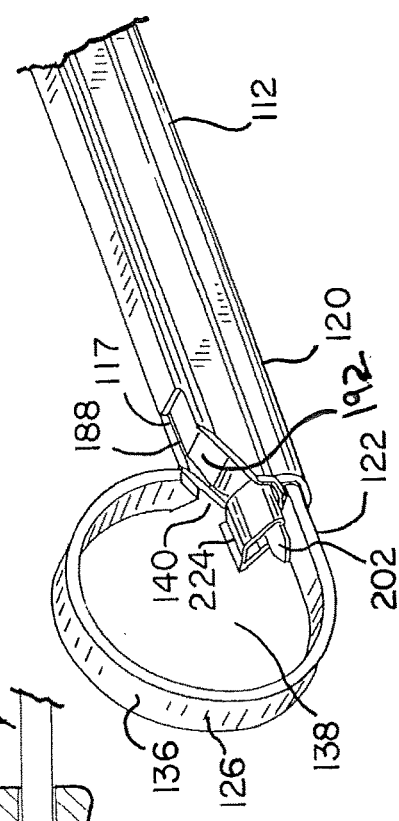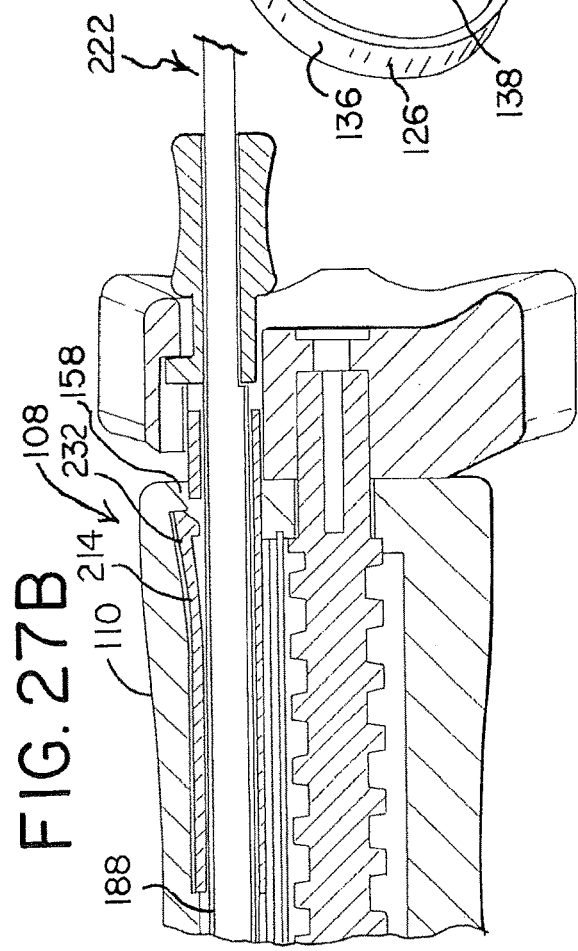

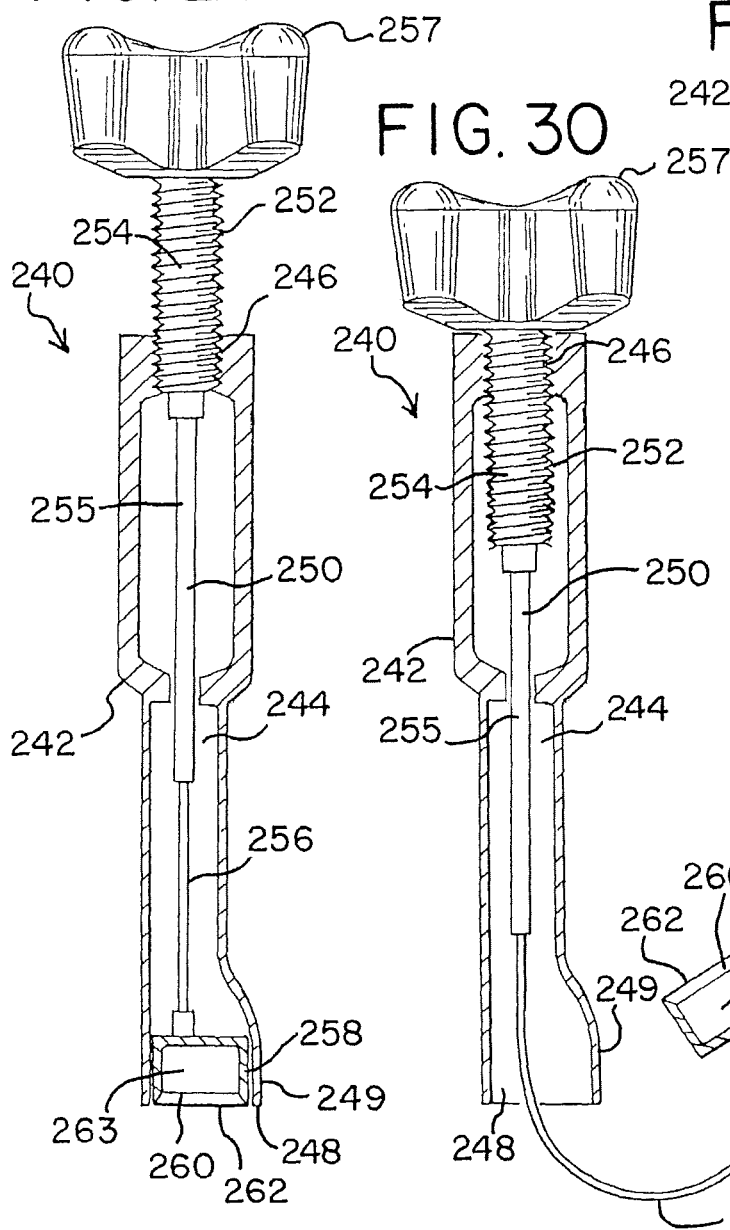

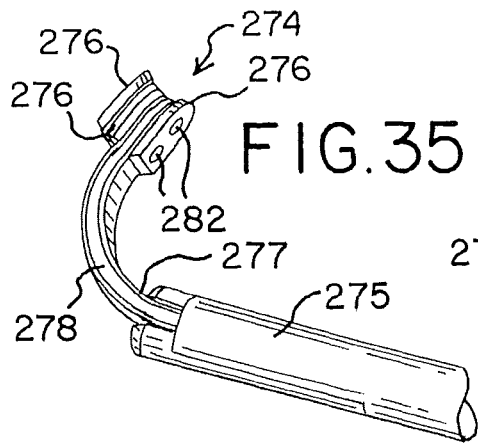
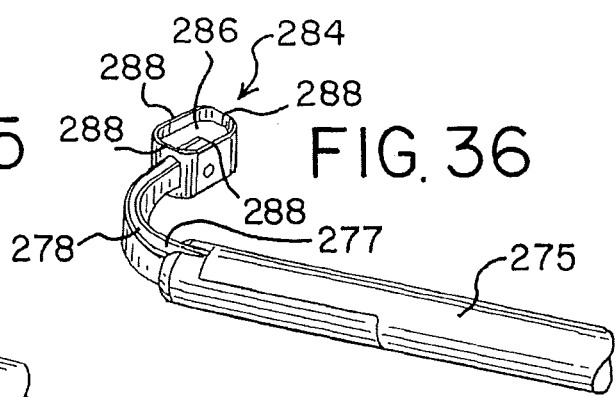
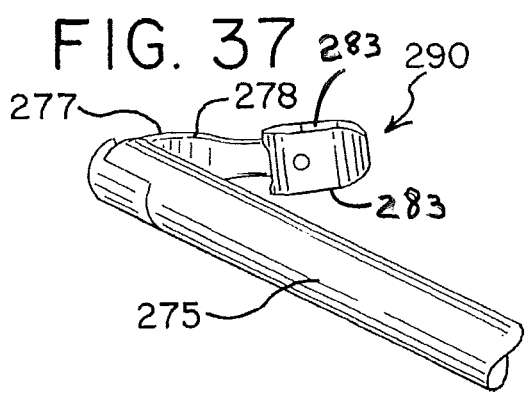
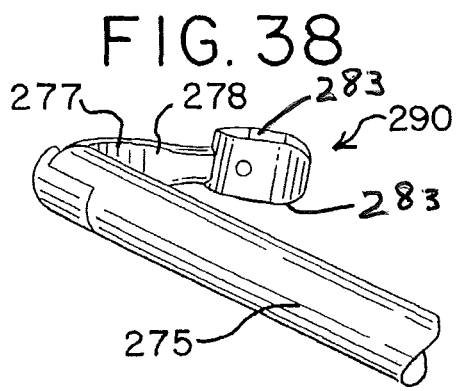
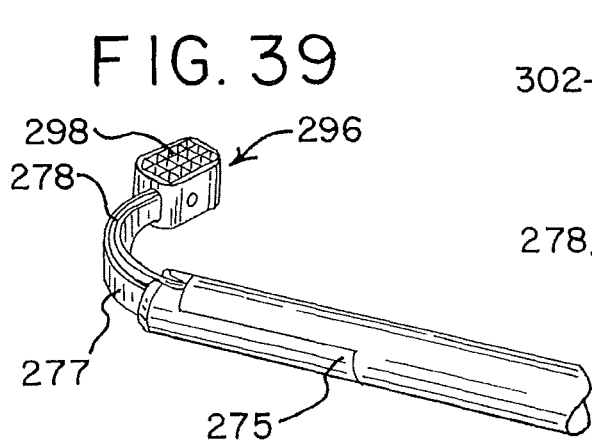
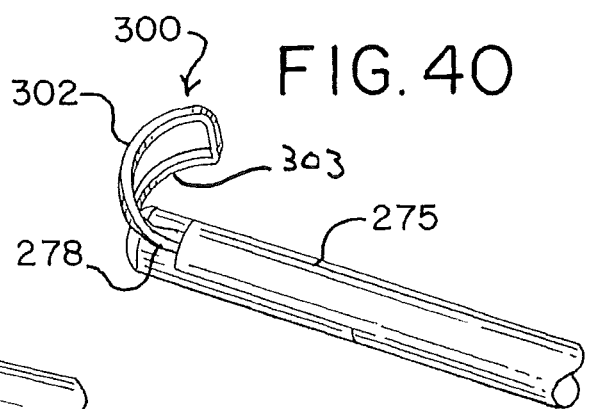

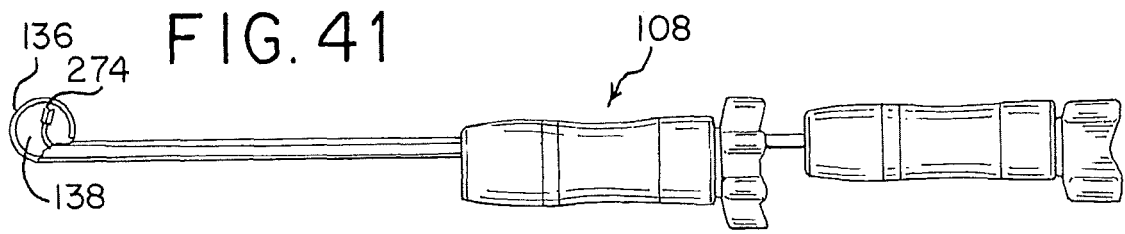
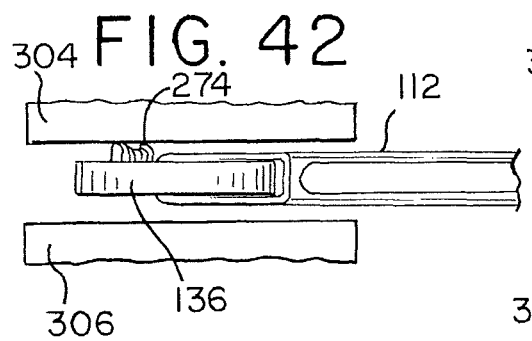
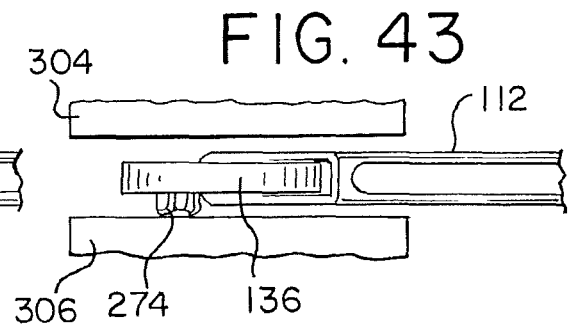
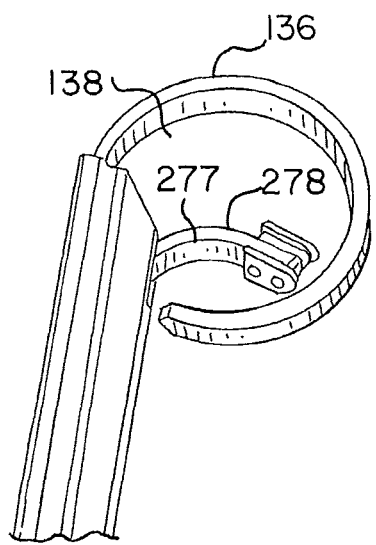
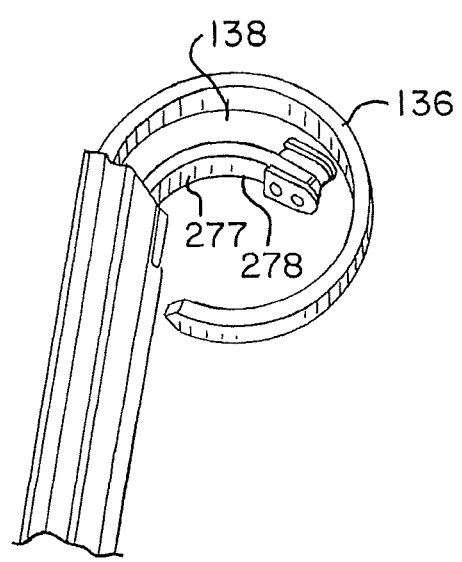

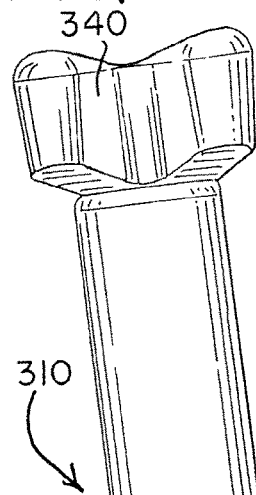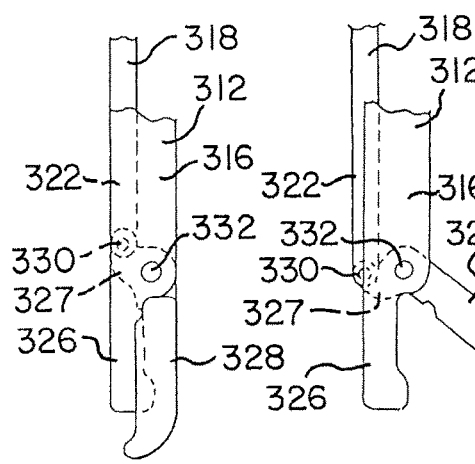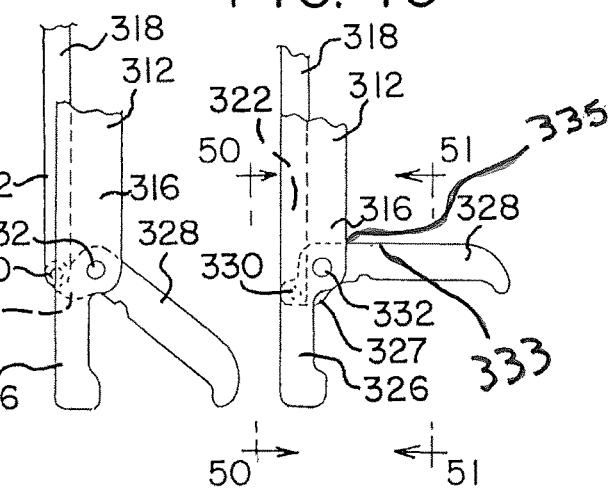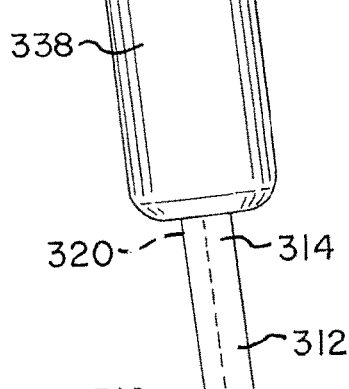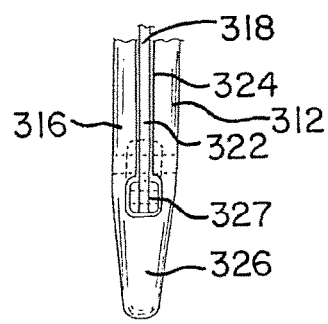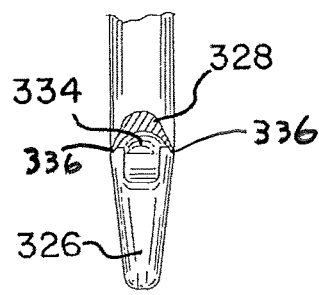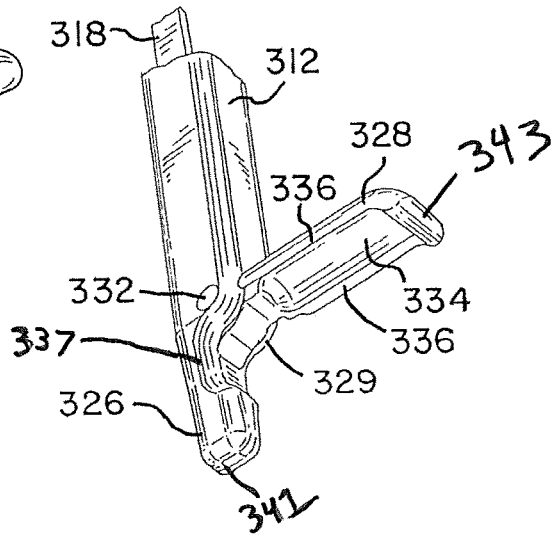

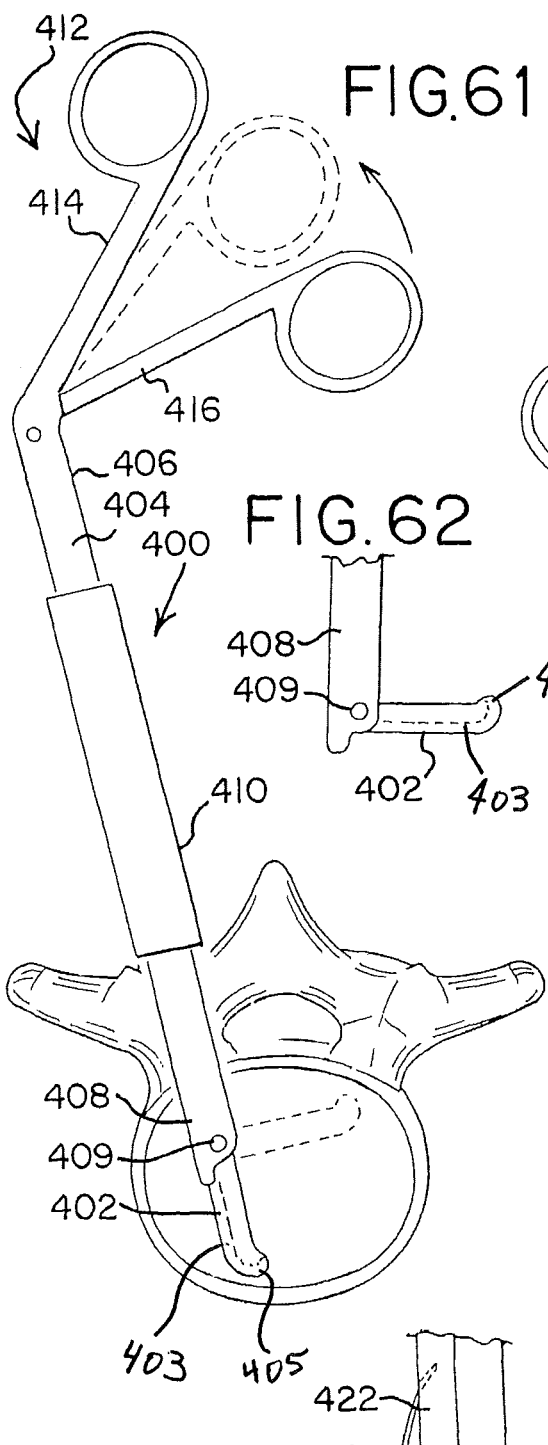

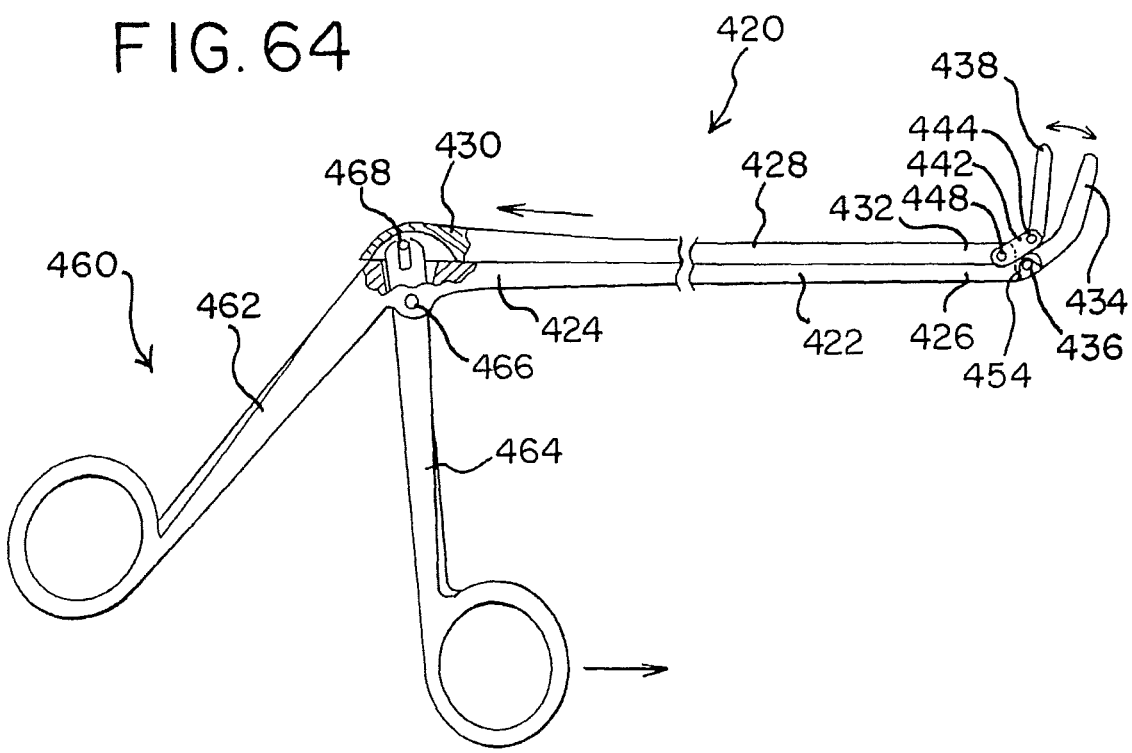
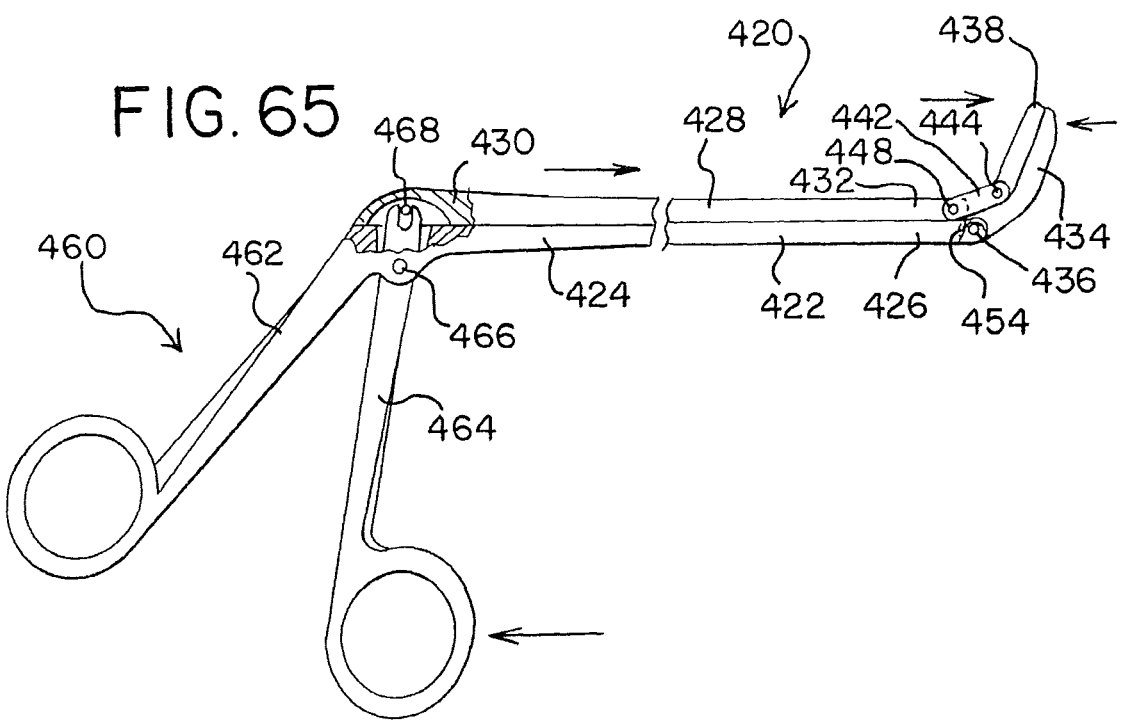

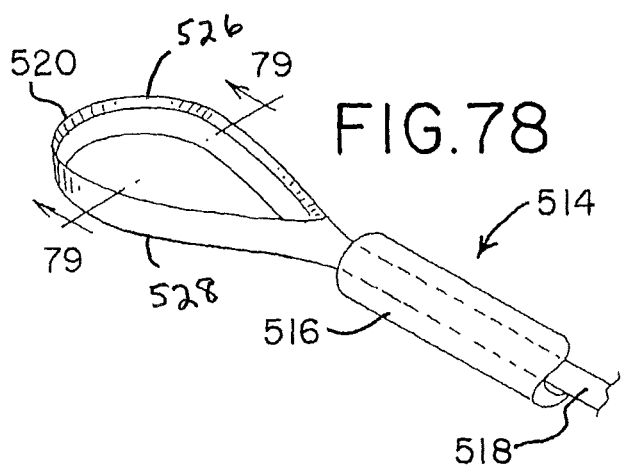
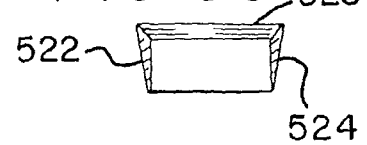
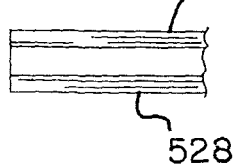
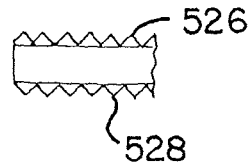
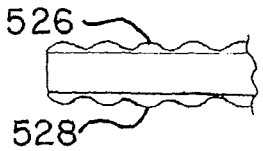
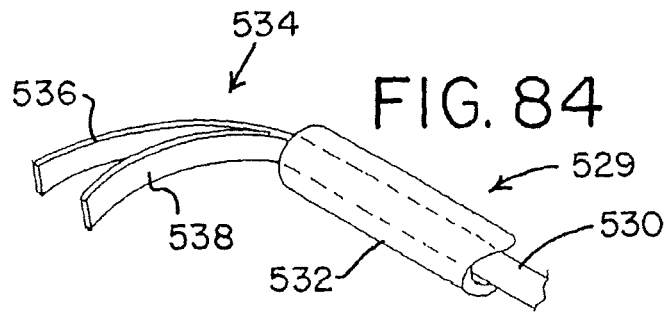
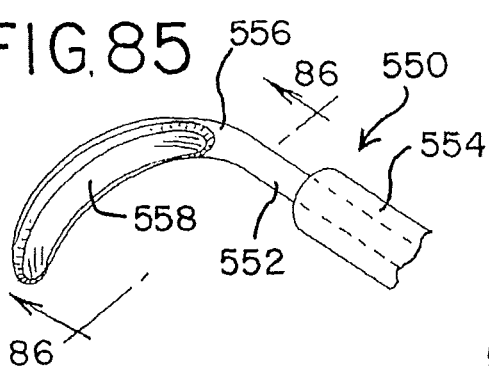
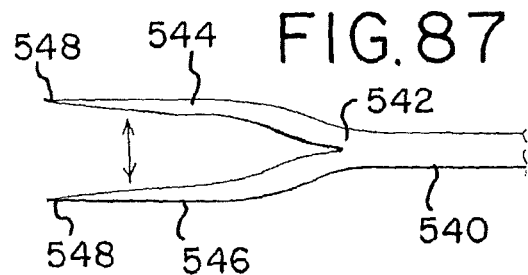
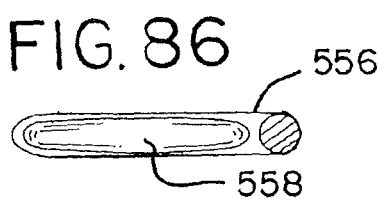
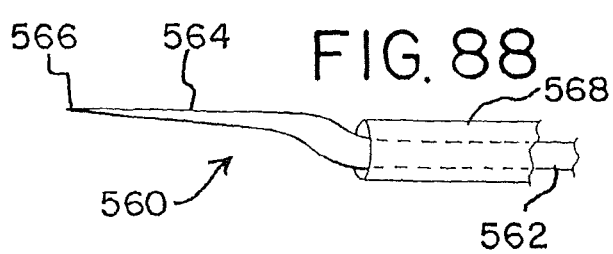

APPARATUS AND METHODS FOR DISRUPTING INTERVERTEBRAL DISC TISSUE

This application is a divisional of U.S. patent application Ser. No. 14/792,956, filed Jul. 7, 2015, which claims the benefit of U.S. Provisional Application No. 62/021,960, filed Jul. 8, 2014, both of which are hereby incorporated herein by reference.

FIELD OF THE DISCLOSURE

The present disclosure generally relates to apparatus and methods employed in surgical procedures to disrupt tissue of a patient, and more particularly, to apparatus and methods that may be utilized in minimally invasive surgical procedures to prepare the intervertebral disc space for other procedures, such as implantation of prosthetics, by forming a barrier around selected tissue to be disrupted within the intervertebral disc space.

BACKGROUND

A major cause of chronic, and often disabling, back pain is herniation or degeneration of an intervertebral disc. The spine is comprised of bony vertebrae separated by intervertebral discs. Each intervertebral disc connects adjacent vertebrae and forms a joint that allows movement of the vertebral column. An intervertebral disc is generally divided into two regions—the nucleus pulposus and the annulus fibrosus. The nucleus pulposus is a gelatinous-like tissue that lies at the center of the disc and provides a cushion between adjacent vertebrae. The annulus is made up of collagen fibers that form concentric lamellae that surround and contain the nucleus pulposus.

There are many causes of intervertebral discs degeneration, which can be broadly categorized as mechanical, genetic and biochemical. Mechanical damage includes herniation in which a portion of the nucleus pulposus projects through a fissure or tear in the annulus fibrosus. Genetic and biochemical causes usually result from changes in the biochemical processes of a disc. Such changes can be attributed to genetic disorders or environmental influences. Degenerative disc condition is commonly caused by a change in the biochemical process of an intervertebral disc. Such degeneration is a progressive process that usually begins with a decrease in the ability of the nucleus pulposus to absorb water. With a loss of water content, the nucleus becomes dehydrated, resulting in a decrease of internal disc hydraulic pressure, and ultimately to a loss of disc height. This loss of disc height can cause the annulus to buckle, eventually resulting in annular fissures and ruptures.

Furthermore, disc height plays an important role in the functionality of the intervertebral disc and spinal column, and changes in disc height can have both local and wider effects. On the local (or cellular) level, decreased disc height may result in increased pressure in the nucleus pulposus, which can lead to a decrease in normal cell operation and an increase in cell death and disintegration. In addition, increases in intra-discal pressure may create an unfavorable environment for fluid transfer into the disc, which can cause a further decrease in disc height.

Decreased disc height also results in significant changes in the larger mechanical stability of the spine. With decreasing height of the disc, the facet joints bear increasing loads and may undergo hypertrophy and degeneration. Decreased stiffness of the spinal column and increased range of motion resulting from loss of disc height can lead to further instability of the spine, as well as back pain.

Several disc defects may be treated by implantation of a prosthetic into the nuclear space of the intervertebral disc. Some procedures that may include insertion of a prosthetic into the disc are spinal fusion and disc repair and replacement. Prior to implantation of most prosthesis, a discectomy is often performed to prepare the nuclear space for implantation of the prosthetic and, when spinal fusion is desired, to facilitate bony fusion between the vertebral bodies. Some implantation procedures may require a total discectomy in which the majority (and usually all) of the volume of the nucleus pulposus is removed. Others may require a partial discectomy in which only a portion of the nucleus pulposus is removed.

Traditionally, discectomy procedures are performed with the use of simple manual instruments, such as curettes, which are cupped scrapers with a variety of end configurations, pituitary rongeurs, which are jaw like gripping or cutting members, and rasps, which include a rough surface that is employed to roughen and scrape endplate tissue of adjacent vertebrae. For a typical posterior surgical approach, an incision is made through the back of a patient and access to the disc space is achieved. The manual instruments are then inserted through the access to the intervertebral disc requiring treatment. The curettes and rongeurs are used to cut, tear, and remove nucleus pulposus tissue one piece at a time, and the rasps are utilized to roughen or scrape the endplates of adjacent vertebrae.

There are some significant limitations associated with performing a discectomy with these manual instruments. For example, since the disc tissue is cut and removed a piece at a time, dozens of repeated cycles of insertion and removal of the traditional instruments are required to remove the desired amount of tissue. The repeated cycles increase the risk of associated nerve damage and the amount of trauma to the surrounding tissue. Additionally, guidance of the traditional instruments is largely controlled by the dexterity of the surgeon, and even with the most skilled surgeons, repeated precise placement of such instruments is a challenge. Furthermore, because of the geometric configuration of traditional instruments and the limited work space associated with intervertebral disc procedures, it can be difficult to adequately remove the required amount of material from the nuclear space. This is particularly the case with a unilateral (one of the more preferred) access of the disc space, where the contralateral half of the disc is significantly more difficult to reach. Finally, surgeons typically use traditional instruments without being able to see the tissue being removed. Thus, the surgeon must be able to distinguish nucleus tissue from annulus tissue and bone tissue by "feel." Thus, if the surgeon has a difficult time distinguishing between these tissues, serious damage can be done to the annulus of the disc or the vertebral bodies.

Other methods and techniques have been developed for performing discectomy procedures. However, these methods and techniques also have limitations and risks associated with their use. Accordingly, there remains a need for improved discectomy devices and methods.

SUMMARY OF DISCLOSURE

The present disclosure provides devices and methods for disrupting tissue within an intervertebral disc space. The devices and methods may include use of a barrier member that isolates tissue to be disrupted from other adjacent or surrounding tissue. The barrier member is inserted into the intervertebral disc space and defines a perimeter of working region which may include tissue selected for disruption. Optionally, the barrier may be inserted under fluoroscope or other visual aid prior to insertion of disruption tools. With the barrier in place, the risk of unintentional disruption of tissue adjacent to the working region is reduced. While such a barrier may be used in any procedure in the disc space, it may be particularly useful in percutaneous minimally invasive procedures wherein the surgeon has limited visibility of the treatment site and is disrupting tissue by feel because the barrier provides a boundary between the working region and other surrounding or adjacent material.

In one aspect, the present disclosure is generally directed to an apparatus for disrupting tissue in the intervertebral disc space that includes a barrier member having a first configuration for insertion into the disc space and a second configuration when deployed within the disc space. The second configuration of the barrier member at least partially defines a perimeter of a working region within the disc space. The apparatus also includes a tissue disruption tool that is insertion into the working region.

In another aspect, a method for disrupting tissue in the intervertebral disc space includes forming a barrier in the intervertebral disc space wherein the barrier at least partially defines a perimeter of a working region within the disc space and disrupting tissue within the working region.

In yet another aspect, an apparatus for disrupting tissue in the intervertebral disc space includes an elongated member including a distal end portion having an arcuate configuration when unstressed. The elongated member is substantially straightened for insertion into the disc space and assumes the arcuate configuration when inserted into the intervertebral disc space. In the disc space, the elongated member defines a perimeter of a working region. The apparatus also includes a tissue disruption tool configured to be inserted into the working region.

In a further aspect, an apparatus for disrupting tissue in the intervertebral disc space includes a first elongated member including a distal end portion having a substantially linear configuration for insertion into the intervertebral disc space and is configured to change to a curved configuration within the disc space to form a barrier that at least partially surrounds disc tissue to be disrupted. The apparatus also includes a second elongated member including a distal end portion wherein the distal end portion of the second elongated member includes a tissue disruptor configured to be inserted into the working region.

In yet another aspect, an apparatus for protecting tissue within the intervertebral disc space includes an elongated member having a distal end portion sized and configured to be deployed into the intervertebral disc space through a percutaneous access. The distal end portion of the elongated member has a curved configuration, when deployed within the intervertebral disc space, which forms a barrier that isolates tissue selected for disruption from selected other tissue, such as selected annulus fibrosis tissue.

In yet another aspect, a tissue disruption tool includes a first elongated shaft having a proximal end portion and a distal end portion and a second elongated shaft having a proximal end portion and a distal end portion and extending generally parallel to the first elongated shaft. The tool also includes a first jaw pivotally attached to the distal end portion of the first elongated shaft and a link pivotally attached to the distal end portion of the second elongated shaft. The tool includes a second jaw being pivotally attached to the link and to the first jaw. The first and second shafts are relatively linearly movable to move the first and second jaws between a first configuration relatively in-line with respect to the elongated shafts and a second configuration extending at an angle relative to the shafts. Additionally, one of the jaws may be biased to the second configuration.

BRIEF DESCRIPTION OF THE FIGURES

In the course of this description, reference will be made to the accompanying drawings, wherein:

FIG. 2A is a top view of one embodiment of a tissue disruption apparatus in accordance with the present disclosure and shown accessing the an intervertebral disc space;

FIG. 2B is a top view of the tissue disruption apparatus of FIG. 2A shown with the distal end portion of the elongated member deployed within the intervertebral disc space to define a working region and a tissue disruption tool partially deployed within the working region;

FIG. 3 is a top view of the tissue disruption apparatus of FIG. 2A shown with the distal end portion of the elongated member and the tissue disruption tool deployed within the intervertebral disc space;

FIG. 4A is a perspective view of one embodiment of an elongated member that forms a barrier in accordance with the present disclosure;

FIG. 4B is a perspective view of another embodiment of an elongated member that forms a barrier in accordance with the present disclosure;

FIGS. 5-7 are perspective views of different configurations of tissue disruptors that may be associated with the distal end portion of the tissue disruption tool;

FIGS. 8A and 8B are top views of one embodiment of a tissue disruption tool in accordance with the present disclosure;

FIG. 9 is a top view of another embodiment of a tissue disruption tool in accordance with the present disclosure;

FIG. 16 is a perspective view of one embodiment of a obturator in accordance with the present disclosure;

FIG. 17A is a perspective view of the tissue disruption apparatus of FIG. 10A shown with the obturator of FIG. 16 inserted therethrough;

FIG. 17B is an enlarged cross-sectional view of the proximal end portion of the housing of the tissue disruption apparatus shown in FIG. 17A;

FIG. 18 is a perspective view of another embodiment of a tissue disruption tool of the present disclosure;

FIG. 19 is an enlarged perspective view of the distal end portion of the tissue disruption tool of FIG. 18;

FIG. 20 is a perspective view of the distal end portion of the tissue disruption tool of FIG. 18 shown in the extended/deployed position;

FIG. 21 is a cross-sectional view of the tissue disruption tool taken along lines 21-21 of FIG. 18;

FIG. 22 is a perspective view of the tissue disruption tool of FIG. 18 shown with the protector located over the tissue disruptor;

FIG. 23 is an enlarged perspective view showing the distal end potion of the tissue disruption tool of FIG. 18 shown with the protector positioned over the tissue disruptor;

FIG. 24 is an enlarged cross-sectional view of the distal end portion of the tissue disruption tool taken along lines 24-24 of FIG. 23;

FIG. 27A is a cross-sectional view of the tissue disruption apparatus of FIG. 10A shown with the elongated member in the extended or deployed configuration and a tissue disruption tool partially deployed into the working region defined by the elongated member;

FIG. 27B is a partial cross-sectional view of the proximal end portion of the housing of the tissue disruption apparatus of FIG. 27A;

FIG. 27C is a perspective view of the distal end portion of the tissue disruption apparatus of FIG. 27A shown with the elongated member in the extended or deployed configuration and a tissue disruption tool partially deployed into the working region defined by the elongated member;

FIGS. 29 and 30 are cross-sectional views of another embodiment of a tissue disruption tool in accordance with the present disclosure;

FIG. 31 is a perspective view of the distal end portion of the tissue disruption tool of FIG. 29 shown with the tissue disruptor partial extended;

FIGS. 32-34 are perspective views of different configurations of tissue disruptors that may be associated with a tissue disruption tool of the present disclosure;

FIGS. 35-40 are perspective views of different embodiments of tissue disruptors that may be associated with a tissue disruption tool of in accordance with the present disclosure;

FIG. 41 is a top view of a tissue disruption apparatus shown with the elongated member and the tissue disruption tool in their respective deployed configurations;

FIGS. 42 and 43 are perspective views of a tissue disruption apparatus schematically shown contacting and disrupting superior and inferior endplate tissue, respectively;

FIG. 44 is a perspective view of a tissue disruption apparatus shown with the elongated member and the disruption tool in their respective deployed configurations;

FIG. 45 is a perspective view of a tissue disruption apparatus shown with the elongated member and the disruption tool in their respective deployed configurations;

FIG. 46 is a perspective view of one embodiment of a tissue disruption tool in accordance with the present disclosure;

FIGS. 47-49 are enlarged top views of the distal end portion of the tissue disruption tool of FIG. 46 showing actuation of the jaws;

FIG. 50 is a cross-sectional view of the distal end portion of the surgical instrument taken along lines 50-50 of FIG. 49;

FIG. 51 is a cross-sectional view of the distal end portion of the tissue disruption tool taken along lines 51-51 of FIG. 49;

FIG. 52 is a partial perspective view of the distal end portion of the tissue disruption tool of FIG. 46;

FIG. 61 is a top view of another embodiment of a tissue disruption tool in accordance with the present disclosure;

FIG. 62 is a top view of the distal end portion of the tissue disruptor of FIG. 61;

FIG. 63 is a side view of another embodiment of a tissue disruption tool in accordance with the present disclosure;

FIG. 64 is a side view of the tissue disruption tool of FIG. 63 shown with the jaws in an open configuration and a portion of the handle cut away;

FIG. 65 is a side view of the tissue disruption tool of FIG. 63 shown with the jaws in a closed position;

FIGS. 68 and 69 are partial side views of another embodiment of jaws of the tissue disruption tool of FIG. 63;

FIG. 78 is a perspective view of another embodiment of a tissue disruption tool in accordance with the present disclosure;

FIGS. 79 and 80 are cross-sectional views of exemplary profiles of the tissue disruption tool of FIG. 78;

FIGS. 81-83 are side views of exemplary profiles of the tissue disruption tool of FIG. 78;

FIG. 84 is a perspective view of another embodiment of a tissue disruption tool in accordance with the present disclosure;

FIG. 85 is a perspective view of another embodiment of a tissue disruption tool in accordance with the present disclosure;

FIG. 86 is a cross-sectional view taken along lines 86-86 of FIG. 85; and FIGS. 87 and 88 are side views of other embodiment of tissue disruption tools in accordance with the present disclosure.

DETAILED DESCRIPTION

The tissue disruption apparatus, tools and methods of the present disclosure may be utilized in any number of surgical procedures to disrupt (cut, scrape, brush, puncture, tear, grasp, extract, remove, etc.) tissue of a patient, but are particularly well suited for performing endoscopic discectomy procedures and preparing intervertebral discs for prosthetic implantation and spinal fusion. For example, such apparatus, tools and methods may be utilized in minimally invasive procedures that are conducted through an access port that has a diameter of between about 0.2 inches (5 mm) and about 1.2 inches (30 mm), and is typically between about 10 mm and about 12 mm. The tissue disruption apparatus and tools disclosed herein may be made from materials or include materials that are visible under x-ray, fluoroscopy or any other suitable imaging system. Such apparatus and tools may also be made of disposable materials, which are configured for single use applications. Alternatively, such apparatus and tools may be configured for multiple or repeat use. The apparatus and tools may be manually operated or operated by an automated apparatus.

Furthermore, the apparatus and tools disclosed herein may be used in combination with each other or may be used by themselves, depending on the procedure and the desired outcome. For example, as will be discussed in more detail below, one of the devices disclosed herein is a barrier member that is inserted into the intervertebral disc space to isolate a working region within the disc space. The barrier member may, for instance, at least partial isolate or enclose intervertebral disc tissue which is selected for disruption and separate such tissue from other tissue adjacent to the treatment area. The present disclosure also discloses various tissue disruption tools that may be inserted into the working region defined by the barrier member to disrupt tissue contained within the working region. The barrier member may be used with any of the tissue disruption tools disclosed herein or any other suitable disruption tools, such as traditional curettes, rongeurs and rasps. Similarly, the disruption tools disclosed herein may be used in combination with any of the barrier members disclosed herein or may be used to disrupt tissue in procedures that do not use a barrier member.

Figure 1A:
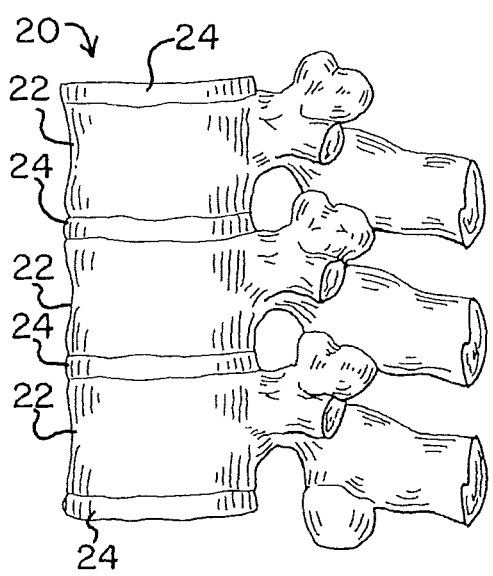
FIG. 1A is a side view of a vertebral column.
Figure 1B:
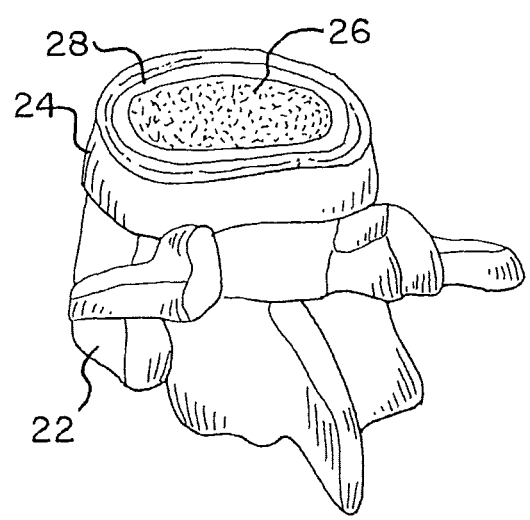
FIG. 1B is a perspective view of an intervertebral disc and its associated inferior vertebra.

FIG. 1 illustrates a section of a healthy vertebral (spinal) column, generally designated as 20. Vertebral column 20 includes vertebrae 22 and intervertebral discs 24 separating adjacent vertebrae 22. Intervertebral discs 24 connect the adjacent vertebra 22 together, providing a joint between the vertebrae that allows movement and flexing of the vertebral column 20. Intervertebral discs 24 also provide a cushion between the adjacent vertebrae 22.

FIG. 2 illustrates a perspective view of one of the intervertebral discs 24 and an associated inferior vertebra 22. The intervertebral disc 24 includes a nucleus pulposus 26 surrounded by an annulus fibrosus 28. The nucleus pulposus 26 is a gelatinous-like material that provides cushioning between adjacent vertebrae. The annulus fibrosus 28 is made up of tougher fiberous material that contains the nucleus pulposus 26 in the nuclear space.

FIGS. 2A-3 illustrate one embodiment of a tissue disruption apparatus 30 that may be inserted through an access cannula 32 in a minimally invasive procedure to perform a discectomy or prepare intervertebral disc 24 for insertion of an implant. In the illustrated embodiment, distal end portion 34 of access cannula 32 is inserted through the annulus fibrosus 28 of disc 24, using a percutaneous posterior approach, to access nucleus pulpous 26. Depending on the procedure, an anterior approach may be employed. A proximal end portion 36 of access cannula 32 may remain outside of the patient. Access cannula 32 includes a proximal end opening 38 and a distal end opening 40 and a lumen (not shown) in communication with openings 38, 40.

The tissue disruption apparatus 30, optionally, includes a first delivery cannula 42 having a proximal end portion 44 defining a proximal end opening 46 and a distal end portion 48 defining a distal end opening 50. A lumen (not shown) extends and is in communication with proximal and distal end openings 46, 50. As shown in FIGS. 2A and 2B, an elongated member 52 is advanceable through delivery cannula 42 and into intervertebral disc 24. Elongated member 52 may be an elongated barrier member that includes a proximal end portion 54 and a distal end portion 56 (FIGS. 2B and 3). Proximal end portion 54 may, optionally, include a knob or handle 58 that may be used to advance and retract the elongated member 52 into and out of the intervertebral disc 26, or advance and retracted elongated member 52 through delivery cannula 42, when one is present.

At least the distal end portion 56 of the elongated member 52 includes a first configuration for insertion/deployment into intervertebral disc 24. In disc 24, distal end portion 56 of elongated member 56 has a second configuration which forms a barrier 60 that at least partially defines a working region 62 within disc 24. Barrier 60 defines at least a portion of a perimeter or boundary of working region 62 for tissue disruption. Depending on the procedure, the tissue to be disrupted may be substantially the entire nucleus pulpous 26, a portion of the nucleus pulpous 26 and/or a portion of the annulus fibrous 28. In one embodiment, barrier 60 surrounds substantially the entire nucleus pulpous. Barrier 60 also separates the tissue to be disrupted from other surrounding tissue. For example, barrier 60 may isolated disc tissue which is selected for disruption from other surrounding tissue.

In the illustrated embodiment, at least the distal end portion 56 of elongated member 52 includes a first substantially linear configuration for advancement through the lumen of delivery cannula 42 for deployment into disc 24. As distal end portion 56 of elongated member 52 is advance into the disc space, it transverses through the disc space and curves into a second, less linear configuration that at least partially surrounds and isolates tissue selected for disruption. Distal end portion may extend to form a barrier that at least partially surrounds ipsilateral and/or contralateral disc tissue. In one embodiment, the distal end portion 56 of elongated member 52 extends contralaterally so as to define a working region that includes at least in part a section of the contralateral area.

In the illustrated embodiment, distal end portion 56 of elongated member 52 changes from a first substantially linear configuration into a second generally arcuate configuration. For example, the generally arcuate shape may be a generally circular shape (e.g., right circular shaped, oval, ellipse, etc.). The second configuration of the distal end portion 56 of elongated member 52 may also be other regular and irregular geometric shapes depending on the desired application. Additionally, the second configuration may be any portion of a geometric shape. For example, the second generally arcuate configuration may be a quarter, half or three-quarters of a circular shape. In one embodiment, the second generally arcuate configuration may be a circular shape that extends almost a full circle (almost 360 degrees), but leaves an opening or open region 64 for ingress and egress of disruption tools. In another embodiment, the distal end portion of 56 of the elongated member 52 may extend in a circular shape and come into contact with one or more of the access cannula 32 or tool delivery cannula 68 so as to fully enclose the working region. In other embodiments, the distal end portion 56 of the elongated member 52 in the second configuration may extend between about 270 degrees and 355 degrees so as to leave an open region to access the working region. In one embodiment, the distal end portion extends between about 345 degrees and 355 degrees.

Referring to FIGS. 4A and 4B, the elongated member may be made of a one-piece construct or multiple-piece construct. In the two-piece construct shown in FIG. 4A, the elongated member 52*a* includes a shaft 53*a* wherein the distal end portion 56*a* of the elongated member 52*a* is attached to the shaft 53*a* by a fastener 66, such as a screw, rivet or any other suitable fastener. In the one-piece construct shown in FIG. 4B, the elongated member 52 is a one-piece strip of material, such as a ribbon of material. In either embodiment, at least the distal end portion 56, 56*a* of the elongated member 52, 52*a* may be made of a shape memory material, such as a shape memory metal or polymer. One such shape memory material is Nitinol. When the distal end portion 56, 56*a* of the elongated member 52, 52*a* is made from a shape memory material, the distal end portion 56, 56*a* may have a predetermined or preset initial shape, such as the illustrated generally circular or ring shape. The distal end portion 56, 56*a* may be constrained into a substantially straight configuration, by for example, the inner surface of the delivery cannula 42. As the distal end portion 56, 56*a* of the elongated member 52, 52*a* is advanced out of the distal opening 50 of cannula 42, it is freed from constraint, which allows the distal end portion 56, 56*a* to return to its initial predetermined shape, thereby forming a barrier in situ that defines a working region 62.

Referring back to FIGS. 2A-3, tissue disruption apparatus 30 may, optionally, include a second delivery cannula 68 for deploying a disruption tool 78. Second delivery cannula 68 includes a proximal end portion 70 having a proximal end opening 72 and a distal end portion 74 having a distal end opening 76. A lumen (not shown) extends through the second delivery cannula 68 and is in communication with the proximal and distal end openings 72 and 76.

Tissue disruption tool 78 may comprise and elongated member 80 that includes a proximal end portion 82 and a distal end portion 84 (FIGS. 2B and 3). The elongated member 80 may be made of metal or polymeric material. The proximal end portion 82 may, optionally, include a knob or handle 86 that may be used to advance and retract the tissue disruption tool 78. Referring to FIGS. 2B and 3, a tissue disruptor 88 is associated with the distal end portion 84 of the tissue disruption tool 78. The tissue disruptor 88 may be configured to cut, scrape, brush, puncture, tear, grasp, extract, and/or remove tissue. Tissue disruptor 88 may be a tissue cutter, scraper, brush, grasper, jaws, curette, rasp or the like. Tissue disruptor 88 may be one-piece with elongated member 80 or may be attached to elongated member 80. In the embodiment illustrated in FIGS. 2B, 3 and 6, tissue disruptor 88 is a brush-like member that includes a plurality of bristles or tines 90. The tissue disruption tool may include any suitable tissue disruptor depending on the desired application. For example, the tissue disruptor 92 shown in FIG. 5 includes a plurality of geometrically shaped members 94 that include sharp edges, blades and points 96. In the illustrated embodiment, the geometrically shaped members 94 are generally rectangular and/or triangular configurations that include sharp edges, blades and points 96 for cutting tissue. As also shown in FIG. 5, the distal tip 98 of the illustrated tissue disruption tool and any of the other disruption tools disclosed herein may be pointed or beveled or otherwise configured for piercing through tissue. In FIG. 7, the tissue disruptor 104 may include bristles or tines 106 that extend in random directions from the disruption tool. Bristles and tines 88 and 106 may be employed to scrape, brush and/or tear tissue and/or also may be employed to capture or grasp tissue to be removed from the disc.

Turning back to FIGS. 2B and 3, distal end portion 84 of the disruption tool 78 may be advanced out of the distal opening 76 of second delivery cannula 68, through the open region 64 of barrier 60 and into the working region 62 defined by barrier 60. As the distal end portion 84 of tissue disruption tool 78 is advanced into working region 62, it may slide or extend along barrier 60, which guides the distal end portion 84 of disruption tool 78 along the perimeter of working region 62. In the illustrated embodiment, distal end portion 84 slides along barrier 60 and the barrier serves as a track that guides distal end portion 84 in a curved path. Furthermore, the tissue disruptor 88 is orientated or faces towards the center of the working region 62.

The tissue disruption tool 78 may be made from a metal or polymeric material that is sufficiently rigid to be advanced through the disc material, but sufficiently flexible to follow along the barrier. In other embodiments, tissue disruption tool 78 may be made from a shape memory material that has a pre-determined curve that may or may not follow along the barrier 60. For example, if the tissue to be disrupted is generally located in the center of working region 62 or more ipsilateral, the curvature of the distal on portion 84 of the disruption tool 78 being made from a shape memory material may be smaller than that of the barrier 60 so that the distal end portion 84 can reach such tissue.

As distal end portion 84 of disruption tool 78 is moved through the working region 62, the tissue disruptor 88 contacts and disrupts tissue. The disruption tool 78 transverses through the working region 62 in any suitable manner to disrupt tissue. For example, the disruption tool 78 may be moved back and forth within the working region 62 to disrupt tissue. The disruption tool also may be rotated or angle within the working region 62. While disruption tool 78 is within the working region, barrier 60 contains tissue disruptor 88 within the working region 62 and protects adjacent tissue outside of working region 62 from inadvertently being disrupted. This is helpful during minimally invasive procedures wherein the surgeon's vision is limited, which increases risk and injury from inadvertent disruption of surrounding tissue. In such minimally invasive procedures, barrier 60 protects surrounding tissue and reduces the risk that such surrounding tissue will be damaged.

After disruption tool 78 has disrupted a desired amount of tissue in working region 62, it is retracted from disc 24 and one or more subsequent tools may, optionally, be inserted into the disc space. The subsequent tools may be the same or similar type of tool or may be a different type of tool. Accordingly, multiple types of disruption tools in any desired order may be inserted and removed from working region 62. For example, cutting tools may first be inserted to cut tissue. Extraction tools may then be inserted to remove tissue. Puncture and scraping tool may be inserted to puncture and/or scrape the surfaces of the endplates within the perimeter of working region 62.

Disruption tool 78 may be retracted from the disc 24 by retracting the distal end portion 84 back into delivery cannula 68 and then removing delivery cannula 68 from access cannula 32, or disruption tool 78 may be retracted through delivery cannula 68, wherein delivery cannula 68 remains in place for insertion of subsequent disruption tools.

FIGS. 8A and 8B illustrate another embodiment of a tissue disruption tool 78a and associated delivery cannula 68a shown positioned within access cannula 32a. In this embodiment, delivery cannula 68a includes a distal end extension 69a that extends beyond the distal end opening 76a of the delivery cannula 68a. Prior to being deployed and while tissue disruption tool 78a and delivery cannula 68a are being inserted through the access cannula 32a, distal end extension 69a may protect tissue disruptor 88a. Furthermore, when tissue disruption tool 78a is made from a shape memory material that has a preset curved configuration, distal end extension 69a may maintain distal end portion 84a of the tool is a substantially straight configuration during insertion through the access cannula 32a. Referring to FIG. 8B, when the distal end portion 84a of tool 78a is deployed, it resumes its predefined configuration. Tissue disruption tool 78a may also include a handle 86a for advancing and retracting the disruption tool into and out of delivery cannula 68a.

As shown in FIG. 9, tissue disruption tool 78b may be of a two-piece construct that includes a shaft 79b wherein the distal end portion 84b of the tissue disruption tool 78b, carrying a tissue disruptor 88b, is attached to shaft 79b. Tissue disruption tool 78b may also include a handle 86b for manipulating the disruption tool. In this embodiment, shaft 79b and distal end portion 84b may be made of the same or different materials. For example, distal end portion 84b may be made from a shape memory material while shaft 79b may be made from a different, non-shape memory material.

Figure 10A:
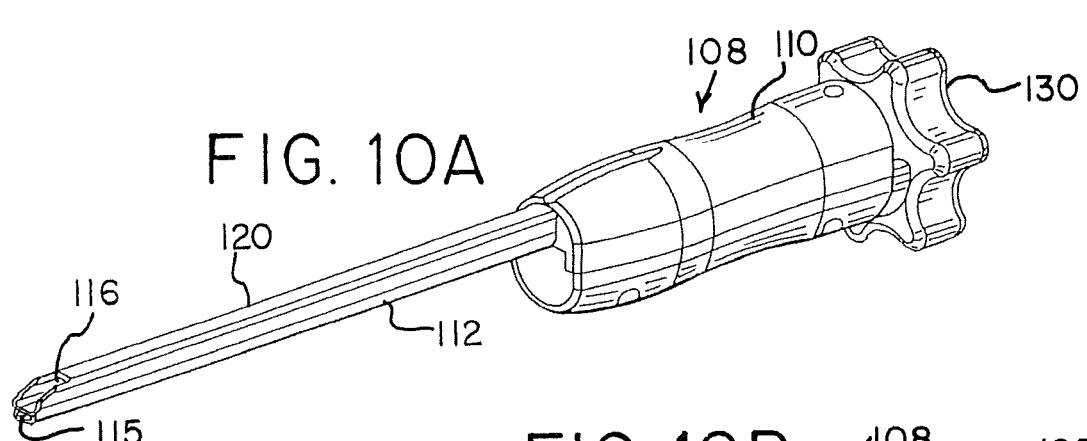
FIG. 10A is a perspective view of one embodiment of a tissue disruption apparatus in accordance with the present disclosure.

FIGS. 10A-15 show a tissue disruption apparatus 108 that includes a housing 110 and at least one delivery cannula 112 extending therefrom. In the illustrated embodiment, the delivery cannula 112 includes a first delivery lumen 114 (FIGS. 10B and 11) and a second delivery lumen 116. In other embodiments, the at least one delivery cannula may be two separate cannulas each having its own lumen. Referring to FIGS. 10A and 10B, delivery cannula 112 includes a proximal end portion 118 that is connected to and extends into the housing 110. Delivery cannula 112 also includes a distal end portion 120 that is configured for insertion into a disc space through an access cannula, similar to that shown in FIG. 2A, or without an access cannula.

Figure 10B:
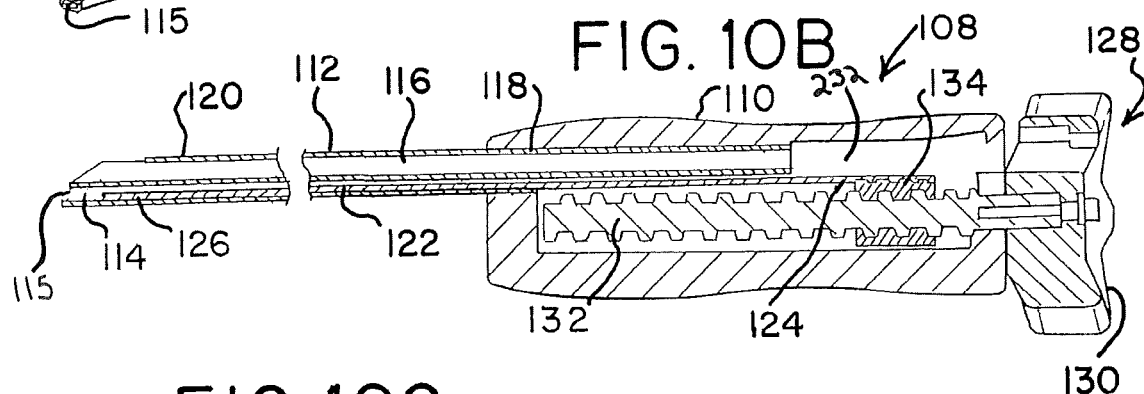
FIG. 10B is a cross-sectional view of the tissue disruption apparatus of FIG. 10A.

In the illustrated embodiment, an elongated member 122 that is configured to form a barrier within the disc space, similar to elongated member 52 discussed above, is located within first lumen 114, as shown in FIG. 10B. Elongated member 122 may come pre-assembled in lumen 114 of tissue disruption apparatus 108. Elongated member 122 includes a proximal end portion 124 (FIG. 10B) and a distal end portion 126. Proximal end portion 124 is operatively connected to any suitable deployment/retraction mechanism or actuator 128 for advancing and retracting elongated member 122 through lumen 114.

In the illustrated embodiment, deployment/retraction mechanism 128 includes a rotatable knob 130 having a threaded post 132 extending therefrom and which rotates therewith. A carriage 134 is located on post 132 and includes internal threads that complement the threads of post 132 such that when the post is rotated in one direction, carriage 134 travels distally along post 132, and when the post is rotated in the other direction, carriage 134 travels proximally along post 132. Proximal end portion 124 of elongated member 122 is attached to carriage 134 such that as the carriage travels distally along post 132, elongated member 122 advances distally through lumen 114 and out distal opening 115. Conversely, as carriage 134 travels proximally along post 132, elongated member 122 is retracted proximally within lumen 114.

Figure 11:
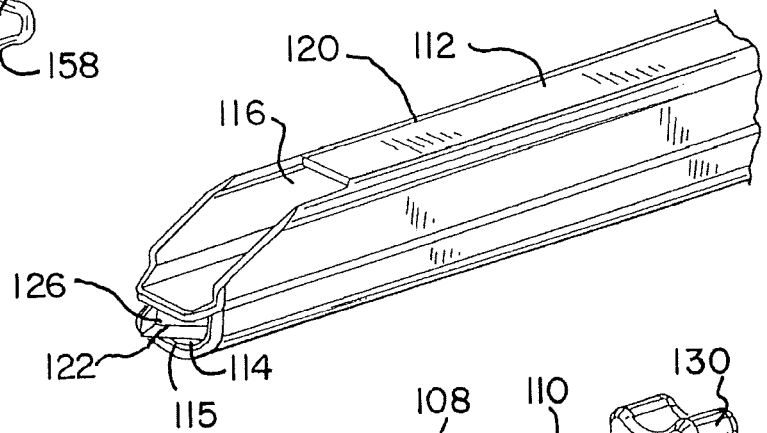
FIG. 11 is an enlarged partial perspective view of the distal end portion of the tissue disruption apparatus shown in FIG. 10A.
Figure 12:
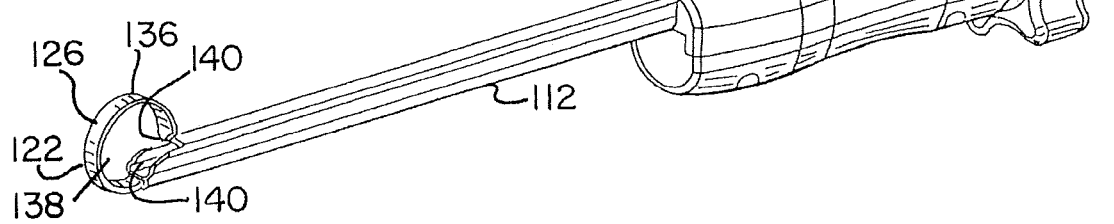
FIG. 12 is a perspective view of the tissue disruption apparatus of FIG. 10A shown with the elongated member in the deployed position.

Referring to FIGS. 10B and 11, in use, distal end portion 120 of deployment cannula 112 may be inserted into the disc space during a minimally invasive procedure. When inserted, distal end portion 126 of elongated member 122 is located within lumen 114 in a first configuration, as shown in FIGS. 10B and 11. In these figures, distal end portion 126 of elongated member 122 is in a generally linear configuration. After distal end portion 120 of deployment cannula 112 is inserted and placed in the desired position, the user rotates knob 130 to advance distal end portion 126 of elongated member 122 out of a distal opening 115 that is in communication with lumen 114. As distal end portion 126 exits out of distal opening 115, it changes into a second configuration, such as the illustrated generally circular configuration, shown in FIG. 12, to form a barrier 136 that defines at least a portion of a perimeter or boundary of a working region 138. The second configuration of elongated member 122 may be similar to and have the same or similar characteristics as the second configuration described above with respect to elongated member 52. As will be discussed in more detail below, barrier 136 may have an open region 140 for the insertion of disruption tools.

Figure 13:
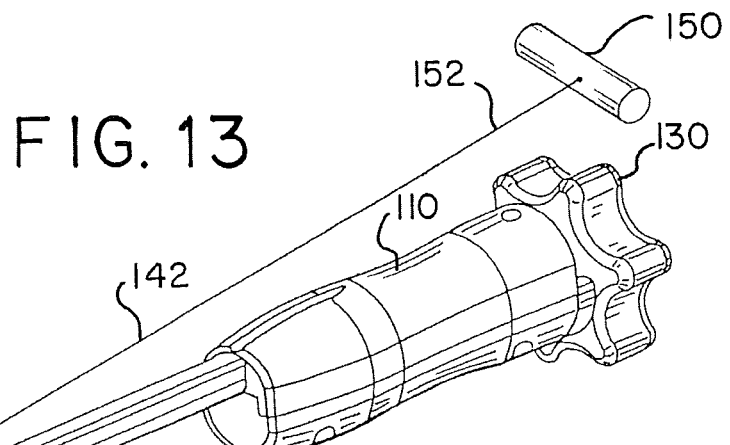
FIG. 13 is a perspective view of another embodiment of a tissue disruption apparatus in accordance with the present disclosure.
Figure 14:
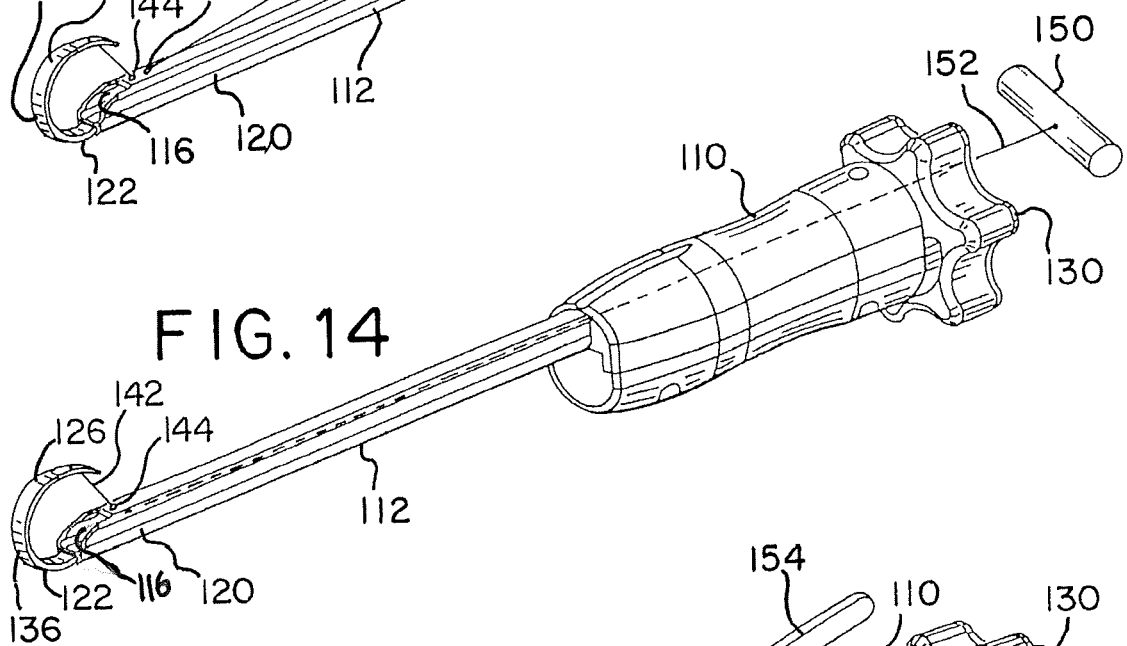
FIG. 14 is a perspective view of another embodiment of a tissue disruption apparatus in accordance with the present disclosure.
Figure 15:
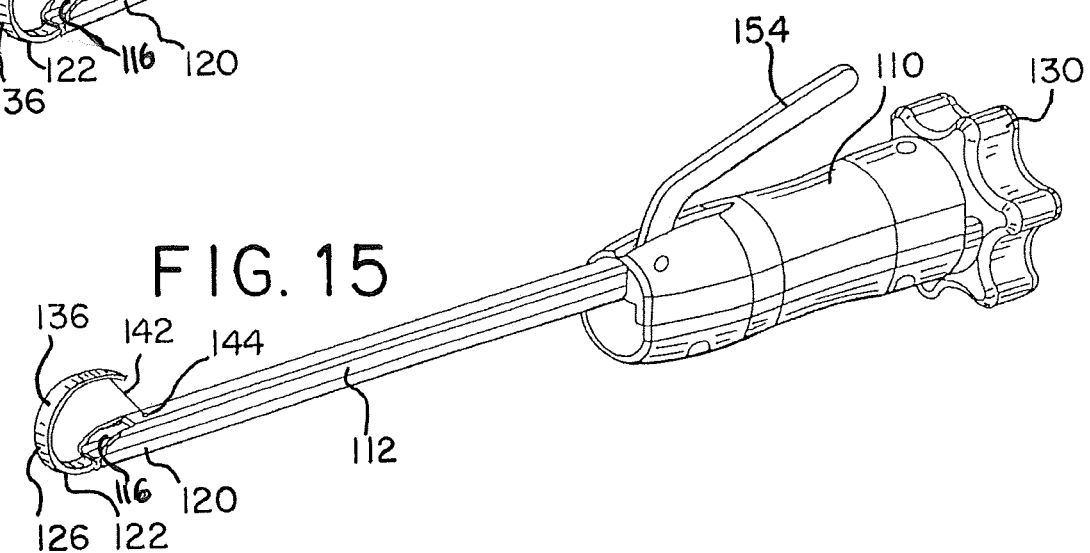
FIG. 15 is a perspective view of another embodiment of a tissue disruption apparatus in accordance with the present disclosure.

Referring to FIGS. 13-15, the tissue disruption apparatus 108 may include a deployment aid or enhancer that may assist in the deployment of distal end portion 126 of elongated member 122. In some patients, the endplates and/or discs may be highly calcified, in which case, distal end portion 126 of the elongated member 122 may encounter resistance as it is advanced through the disc space. Such resistance may impede insertion of distal end portion 126 into the disc space and also may impede the ability of distal end portion 126 to form the desired or pre-set shape of the barrier 136. As illustrated in FIGS. 13-15, the deployment enhance may include a pull wire, such as tether 142, that may be pulled or otherwise tensioned to assist in advancing distal end portion 126 of the elongated member 122 through the disc space and/or forming distal end portion 126 into a desired shape barrier 136. In FIGS. 13-15, tether 142 is attached to distal end portion 126 of the elongated member 122. Tether 142 passes through an opening 144 in distal end portion 120 of delivery cannula 112 so that when it is pulled or otherwise tensioned, it pulls or guides the distal tip 146 of the elongated member 122 toward distal end portion 120 of delivery cannula 112 to assist traversing distal end portion 126 of elongated member 122 through the disc space and/or to assist forming it into the desired shape. In the illustrated embodiment, tether 142 assists in forming the distal end portion of the elongated member into a circular configuration.

In FIG. 13, tether 142 may extend through a first opening 144 and into lumen 16 of delivery cannula 112 and then extend out through a second opening 148. Tether 142 extends proximally outside of the tissue disruption apparatus 108 and a handle 150 is associated with the proximal end portion 152 of tether 142. When in use, tether 142 may extend from the disc space through the access channel with handle 150 located outside of the proximal end opening of the access channel so that the user may grasp and pull the handle 150 during use.

In FIG. 14, tether 142 extends through opening 144 in delivery cannula 112, through lumen 116 and out of the proximal opening of housing 110. In FIG. 15, tether 142 may extend through opening 144 in delivery cannula 112 and through lumen 116. The proximal end portion of tether 112 may be attached to an actuator 154 that is actuated by the user to place tension on the tether. In the illustrated embodiment, the actuator 154 is a level pivotally attached to the housing 110 wherein the leveler is moved to place tension on the tether.

Figure 10C:
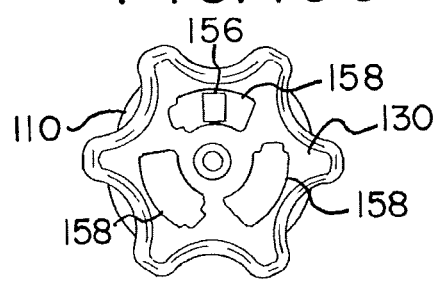
FIG. 10C is an end elevational view of the tissue disruption apparatus of FIG. 10A.

As discussed above, second lumen 116 is configured to receive working tools therethrough. Referring to FIG. 10C, housing 110 may include an opening 156 for receiving a tool therethrough and into second lumen 116. In the illustrated embodiment, knob 130 may also include openings 158 therethrough so that the tools may access opening 156.

FIG. 16 illustrates one exemplary embodiment of an obturator 160 that may be inserted into and through lumen 116 (FIG. 10B). Obturator 160 has an elongated shaft 162 having a proximal end portion 164 and a distal end portion 166. A hub 168 for handing obturator 160 and releasably connecting obturator 160 to housing 110 of the tissue disruption apparatus 108. Referring to FIGS. 17A and 17B, obturator 160 may be inserted through opening 158 in knob 130 and opening 156 in housing 110 (FIG. 10C) to insert shaft 162 into and through lumen 116. As shown in FIG. 17A, the distal tip 170 of obturator 160 is pointed and/or sharp and extends out of opening 117 of lumen 116 and distally of the distal end portion 120 of cannula 112. Obturator 160 may be employed to assist in inserting cannula 112 into and through tissue in that distal tip 170 of obturator 160 may be used to pierce tissue as cannula 112 is inserted into and through the tissue. For example, cannula 112, with obturator 160 located therein, may be inserted percutaneously through the skin and soft tissue without the need for a previously inserted access cannula.

Additionally, hub 168 may include a releasable locking mechanism that mates with knob 130 to releasably lock obturator 160 to tissue disruption apparatus 108. Referring to FIG. 17B, the locking mechanism may include a depressible lever 172 in which the distal end 174 thereof is pivotally connected to hub 168. The proximal end 176 is biased upward to a locked position by a biasing member 178, such as the illustrated spring. Lever 172 includes a surface 180 which contacts a surface 182 of knob 130 in an opposed relationship to lock obturator 160 into position within tissue disruption apparatus 108. Locking obturator 160 to knob 130 assists in maintaining obturator 160 in position as cannula 112 is inserted and pushed through tissue. The proximal end surface 184 of hub 160 also may be flat or otherwise conducive to striking with a hammer or mallet to aid in inserting cannula 112 into and through tissue. Once cannula 112 is the desired position, proximal end 176 of lever 172 may be depressed to disengage surface 180 from knob 130. Obturator 160 may then be removed from tissue disruption apparatus 108 and other tools may be inserted into and through lumen 116.

FIGS. 18-24 show one embodiment of a tissue disruption tool 186 that may be used with tissue disruption apparatus 108. Turning to FIGS. 18 and 21, tissue disruption tool 186 includes a shaft 188 having a proximal portion 190 and a distal end portion 192. Shaft 188 also includes a lumen 194 extending therethrough. An elongated member 196 extends through lumen 194. Elongated member 196 has a proximal end portion 198, an intermediate portion and a distal end portion 202. Referring to FIGS. 18 and 22, proximal end portion 198 of elongated member 196 extends proximally out of proximal end portion 190 of shaft 188 and distal end portion 202 of elongated member 196 extends distally out of distal end portion 192 of shaft 188. A handle 204 is associated with proximal end portion 198 of elongated member 196. Handle 204 may be grasped by a user to move elongated member 196 distally and proximally with lumen 194 of shaft 188. Furthermore, elongated member 196 may include a stop (not shown) that limits the movement of the elongated member 196 within the lumen 194 of shaft 188. Such a stop may include a post (not shown) which extends from elongated member 190 into channel 195 of shaft 188. The stop may abut the distal end 197 (FIGS. 19 and 20) of channel 195 to limit the distal advancement of the elongated member 196. Channel 195 may also be used to access and assemble elongated member 196 when it is of a multi-piece construct. For example, channel 195 may be accessed to attach pieces of the elongated member 196 to form the same.

Referring to FIGS. 19 and 20, a tissue disruptor 206 is associated within with distal end portion 202 of elongated member 196. Tissue disruptor 206 may be any tissue disruptor disclosed herein or any other suitable tissue disruptor or end effector. In the illustrated embodiment, tissue disruptor 206 includes three hollow members 208 having generally square profiles. The hollow members include edges 210 for cutting tissue. Distal end portion 202 of elongated member 196 may be made of a material that has sufficient flexibility to bend or curve when inserted along the barrier member, or may be made of a shape memory material that has a preset shape. Comparing FIGS. 19 and 20, handle 204 may be used to move elongated member 196 between an initial retracted position shown in FIG. 19 and an extended or deployed position shown in FIG. 20.

Tissue disruption tool 186 may include a protector 214 which protects tissue disruptor 206 prior to insertion into tissue disruption apparatus 108 (FIG. 10A). Referring to FIGS. 22-24, protector 214 may be a sleeve having a lumen for receiving the shaft 188 therethrough. In these figures, protector 214 is shown in an initial position extending over and covering tissue disruptor 206. Referring to FIGS. 18 and 22, protector 214 and shaft may be relatively moveable to one another such that protector 214 may be moved on shaft 188 from the initial distal position to a proximal position. Referring to FIGS. 23 and 24, protector 214 may include a tab 216 that has a projection 218 that projects into a slot 220 of the distal end portion 192 of shaft 188 to releasably lock protector 214 in the initial position. As will be described in more detail later, when tissue disruption tool 186 is inserted into tissue disruption apparatus 108, protector 214 will be released and shaft 188 will pass through it to move protector 214 into a more proximal position shown in FIG. 18.

Figure 25:
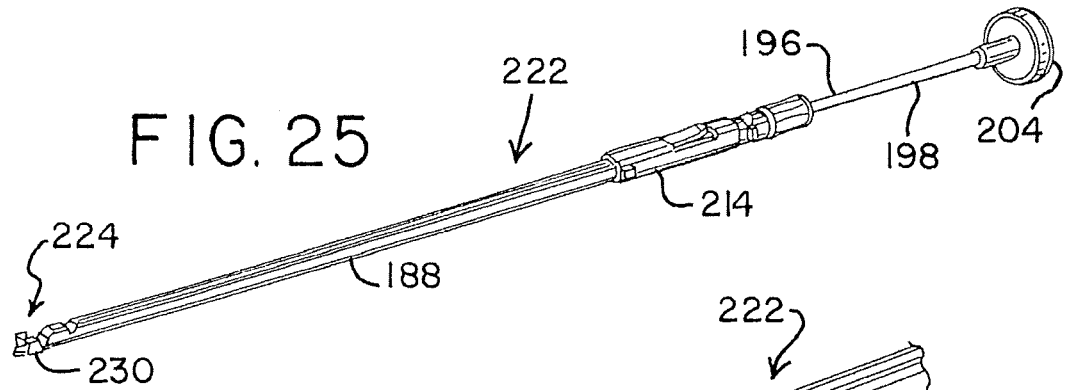
FIG. 25 is a perspective view of another embodiment of a tissue disruption tool in accordance with the present disclosure.
Figure 26:
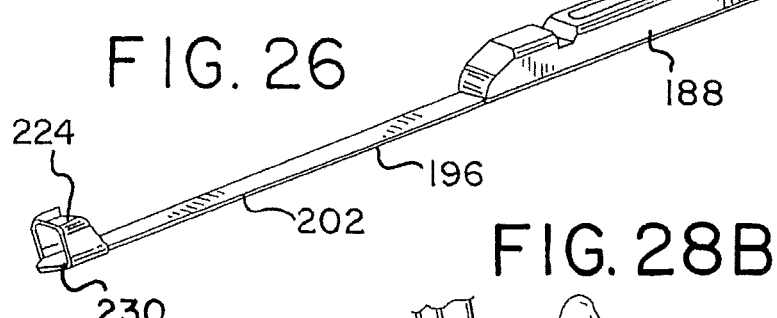
FIG. 26 is an enlarged perspective view of the distal end portion of the tissue disruption tool of FIG. 25.

FIGS. 25 and 26 illustrate another embodiment of a tissue disruption tool 222, which includes substantially the same features and functions in substantially the same manner as tissue disruption tool 186. Tissue disruption tool 222 includes a disruptor 224 associated with distal end portion 198 of elongated member 196. Disruptor 224 includes a single hollow cutting element 230 that has a generally square profile and cutting edges 230.

Referring to FIGS. 27A-27C, illustrate the use of tool 222 with apparatus 108. Cannula 112 of tissue disruption apparatus 108 is inserted into the disc space and distal end portion 126 of elongated member 122 is deployed to form a barrier 136. As discussed above, the distal end portion 126 of elongated member 122 may extend almost a full 360 degrees. In one embodiment, the distal end portion 126 comes into contact with the distal end portion 192 of the shaft and/or the distal end portion 120 of the delivery cannula 112 to fully enclose the tissue to be disrupted. After the barrier 136 has been deployed, a tissue disruption tool, such as any of the tissue disruption tools disclosed herein or any other suitable tissue disruption tool, is inserted into the lumen 116 of tissue disruption apparatus 108 (FIG. 10B). In the illustrated embodiment, tissue disruption tool 222 is shown inserted into tissue disruption apparatus 108. Tissue disruption tool 222 may be inserted through opening 158 in knob 130 and distal opening 156 of housing 110 (FIG. 10C). Referring to FIG. 27B, when tissue disruption tool 222 is inserted into opening 156 of housing 110, protector 214 enters and is maintained in a cavity 232 defined by housing 110. As shaft 188 is advanced through housing 110, protector 214 enters and remains in cavity 232 (FIG. 10B). As shaft 188 is further advanced through housing 110, the angled surface of projection 218 of protector 214 contacts angled surface 219 of distal end portion 192 of shaft 188 (FIG. 24) to release protector 214 and allow shaft 188 to pass through protector 214 and into the lumen 116 of cannula 112.

Figure 28B:
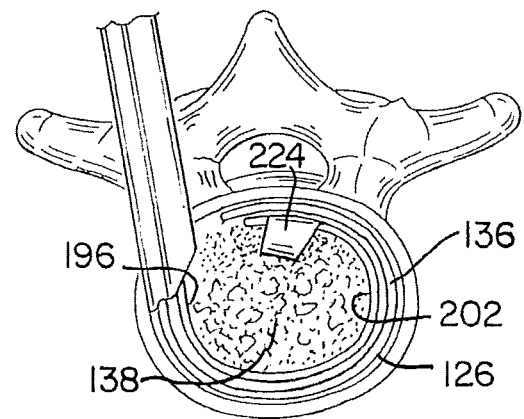
FIG. 28B is a top view of the tissue disruption apparatus of FIG. 28A shown deployed within an intervertebral disc space.
Figure 28A:
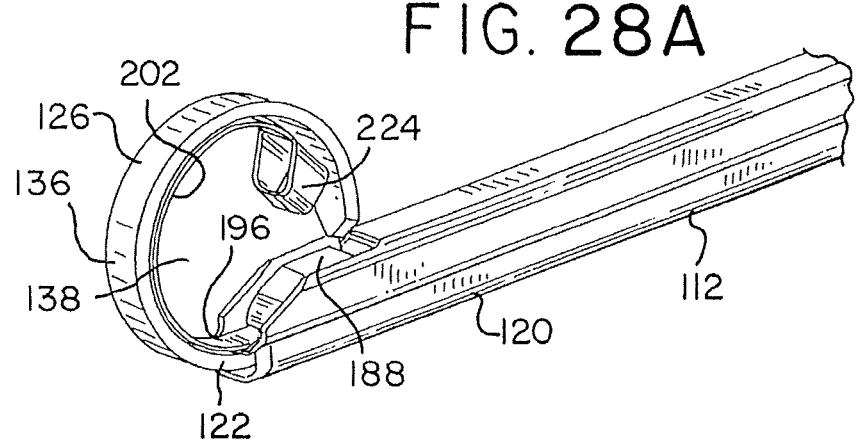
FIG. 28A is a perspective view of the distal end portion of the tissue disruption apparatus of FIG. 27A shown with the elongated member in the extended or deployed configuration and the tissue disruption tool deployed within the working region.

As shown in FIG. 27C, when tissue disruption tool 222 is fully inserted into lumen 116, the distal end 192 of shaft 188 of tissue disruption tool 222 aligns with opening 117 of cannula 112 and distal end portion 202 and associated disruptor 224 partially enter working region 138 through opening 140 of the barrier 136. Referring to FIGS. 28A and 28B, the user uses handle 204 (FIG. 25) to advance distal end portion 202 and associated disruptor 224 into working region 138. In the illustrated embodiment, distal end portion 202 has sufficient flexibility to curve along barrier 136 and sufficient rigidity to traverse and disrupt tissue within barrier 136. After elongated member 196 has been advanced, the user uses handle 204 to retract distal end portion 202 back into the lumen of the shaft 188. Tissue disruption tool 222 may be removed from tissue disruption apparatus 108 and a similar type or different type of tissue disruption tool may be inserted and the process may be repeated. After the selected tissue has been disrupted, tissue disruption apparatus 108 may be removed from the patient.

FIGS. 29-40 illustrate various tissue disruption tools that may be used in combination with any of the barriers disclosed herein. Such tissue disruption tools may also be used in procedures that do not include the use of a barrier. Additionally, the disruption tools may be used to disrupt intervertebral disc and/or endplate tissue.

Referring to FIGS. 29-31, tissue disruption tool 240 includes a cannula 242 which defines a lumen 244. Cannula 242 includes a proximal end opening 246 and a distal end opening 248. A shaft or elongated member 250 is located within the lumen 244. The proximal end 252 of shaft 250 includes a threaded portion 254 which mates with threads in proximal end opening 246 of cannula 242. A knob 257 may be associated with threaded portion 254 and used to rotate threaded portion 254 within opening 246. Threaded portion 254 of shaft 250 may be rotatable connected to an intermediate portion 255 of shaft 250 so that threaded portion 254 may be rotated relative to the remaining portions of shaft 250.

At the distal end portion 256 of shaft 250 is a tissue disruptor 258. In the illustrated embodiment, tissue disruptor 258 is a generally open cubicle member having an opening 260 defined by sharp edges 262. Tissue disruptor 258 includes a cavity 263 that may act as a scoop for scooping tissue. The distal end 256 of shaft 250 and associated tissue disruptor 258 may be advanced out of distal end opening 248 by rotating knob 257. Rotating knob 257 in one direction causes shaft 250 to advance distally and rotating knob 257 in the other direction causes shaft 250 to retract proximally. In other embodiments, the disruptor may be advanced and retracted by other mechanism such as a ratcheting or rack and pinion system or a handle and worm gear. Distal end 249 of cannula 242, optionally, may be enlarged to accommodate the profile of tissue disruptor 258.

Distal end portion 256 of shaft 250 may be made of a shape memory material that has a pre-set curved shape when unrestrained or may be made of a flexible material that curves along a barrier when advanced therealong. Additionally, the distal end portion 256 of elongated member 250 may have a radius of curvature between about 5 mm and about 50 mm. In one embodiment, the radius of curvature is sufficient so that the disruptor 258 may reach contralateral material. For example, the radius of curvature may be about 25 mm. The length of the distal end portion 256 may be between about 4 inches and about 12 inches.

Disruptor 258 may be inserted into the disc space to clear loose or partially detached nucleus tissue from the disc space before an implant is inserted into the space. Additionally, sharp edges 262 may contact and separate tissue from the inferior and superior endplates. The profile of disruptor and the curvature of distal end portion 256 of elongated member 250 may be selected to match or mimic the insertion of an implant, so that disruption tool 240 may be used to test that the removal of tissue (e.g., discectomy) is adequate for insertion or the implant.

FIGS. 32-34, show exemplary embodiments of tissue disruptors that may be associated with any of the tissue disruption tools disclosed herein. Referring to FIG. 32, tissue disruptor 264 has a generally round hollow profile that is generally cylindrically shaped. Tissue disruptor 264 includes a round sharpened edge 266 configured to disrupt tissue. The disc material may pass through the opening in the disruptor 264 as it is advanced through the disc. While the illustrated profile is round, the disruptor may have any hollow profile having wherein one or both ends are open. FIG. 33 illustrates a tissue disruptor 268 that has a generally triangular profile having an open end defined by sharpened edges 270.

FIG. 34 illustrates a tissue disruptor 272 which has a generally spade-like shape including an edge for cutting 273 and piercing tissue. Edge 273 may be particularly configured for disrupting tissue of the endplates and the edge may provide a down bite (surfaces configured to scrape or otherwise disrupt tissue when the disruptor is advanced) or an up bite (surfaces configured to scrape or otherwise disrupt tissue when the disruptor is retracted). Additionally, one side of the disruptor 272 or the other may be particularly suited for scraping the superior or inferior endplate.

FIGS. 35-40 illustrate additional tissue disruption tools that may be particularly well suited for disrupting endplate tissue, but may also be employed to disrupt disc tissue. The tools illustrated in these figures may include a delivery cannula 275 and a shaft 277 having a tissue disruptor associated with a distal end portion 278 of shaft 277. Similar to the above discussed embodiments, the distal end portion 278 of shaft 277 may have a radius of curvature and/or length of distal end portion 256 of shaft 250. FIG. 35 shows a tissue disruptor 274 that includes a generally ogive or oblong shape. Disruptor 274 may be formed from a plurality of layers 276 stacked on both sides of the distal end portion 278 of shaft 277 and attached by fasteners 282. Each of the layers 276 may include edges that are sharp or otherwise configured to cut, scrape or puncture endplate tissue. FIG. 36 shows a tissue disruptor 284 that has a generally rectangular cuboid shape. Tissue disruptor 284 may include upper and/or lower cavities 286 and edges 288 that may be sharp or otherwise configured to cut, scrape or puncture endplate tissue. FIGS. 37 and 38 show a tissue disruptor 290 that is generally ogive or oblong shaped and includes edges 283 for scraping or cutting endplate tissue. In FIG. 37, tissue disruptor 290 is angled or titled upward relative to distal end portion 278 of shaft 277. The upward angle may be particularly suited for disrupting tissue of a superior endplate. In FIG. 38, tissue disruptor 290 is angled or titled downward relative to distal end portion 278 of shaft 277. This downward angle may be particularly well suited for disrupting tissue of an inferior endplate. FIG. 39 shows a tissue disruptor 296 that has a generally rectangular cuboid or cubic shape. The upper and/or lower surfaces 298 may include a texture configured for disrupting endplate tissue. For example, the surfaces may include spikes or serrations. FIG. 40 shows a looped tissue disruptor 300 that may include upper edge 302 and lower edge 303 that may be sharp or otherwise configured to contact and, disrupt endplate tissue. In any of the above discussed disruptors, the surface may be particularly configured to provide a down bite or an up bite.

FIGS. 41-45 show tissue disruptor 274 being used with tissue disruption apparatus 108 and deployed within working region 138 defined by barrier 136. It will be understood that any of the tissue disruptors shown in FIGS. 35-40 may be used with tissue disruption apparatus 108 in a similar manner. In FIGS. 42 and 43, cannula 112 of the tissue disruption apparatus 108 is inserted into the disc space and between superior and inferior end plates 304, 306 and elongated member has been deployed to form barrier 136. FIG. 42 shows tissue disruptor 274 being rotated or angled upward to disrupt tissue of superior endplate 304 within the working region defined by barrier 136. FIG. 43 shows tissue disruptor 274 being rotated or angled downward to disrupt tissue of inferior endplate 306 within the working region. In both instances tissue disruptor 274 may manipulated to contact and scrape endplate tissue by back and forth and rotational movement.

As discussed above, distal end portions of the tissue disruption tools may have configurations that are particularly conducive for reaching a more contralateral or ipsilateral region. Turning to FIGS. 44 and 45, FIG. 44 shows an embodiment wherein distal end portion 278 of shaft 277 has a tighter radius of curvature. FIG. 45 shows an embodiment wherein distal end portion 278 of shaft 277 has a larger radius of curvature.

FIGS. 46-52 illustrate another embodiment of a tissue disruption tool 310 that may be used with the tissue disruption apparatus disclosed herein or may be used as a tool on its own. Furthermore, tissue disruption tool 310 may be particularly well suited for scraping endplate tissue. Tissue disruption tool 310 may include a first elongated shaft 312 having a proximal end portion 314 and a distal end portion 316 and a second elongated shaft 318 having a proximal end portion 320 and a distal end portion 322. The second shaft 318 may be positioned in an axially extending channel 324 of the first shaft 312, as shown in FIG. 50. A first jaw 326 is attached or extends from the distal end portion 316 of the first shaft 312. A second jaw 328 includes a portion 327 that extends through a slot 329 (FIG. 52) in first shaft 312 so that it can be pivotally attached to the distal end portion 322 of the second shaft 318 at a first joint 330, such as a joint that uses a pivot pin. The second jaw 328 is also pivotally attached to the first jaw 326 or the first shaft 312 at a second joint 332, such as a pivot pin joint, that is at a location distal of the first joint 330 when the jaws are in a closed position.

The first and second shafts 312, 318 are moveable linearly relative to one another and when the second shaft 318 is moved distally relative to the first shaft 312, the second jaw 328 pivots relative to the second shaft 318 at joint 330 and pivots relative to the first shaft 312 or jaw 326 at joint 332, thereby moving the second jaw 328 away from the first jaw 326 and placing the jaws in an open position. In the fully opened position, the rear wall 333 of jaw 328 may contact the first shaft at 335. Such contact acts as a stop to prevent movement beyond a set maximum open position. In the illustrated embodiment, the maximum open position is 90 degrees, which could be greater or smaller depending on the procedure. The stop assists in preventing the jaw from damaging other tissue. When the second shaft 318 is moved proximally relative to first shaft 312, the second jaw 328 moves toward the first jaw 326, thereby placing the jaws in a closed position.

In the illustrated embodiment, the second jaw 328 is oversized and bigger than the first jaw 326. As shown in FIG. 46, the oversized second jaw 328 may be helpful in reaching contralateral tissue. As shown in FIGS. 51 and 52, moveable jaw 328 may have sharp edges 336 for that may contact and scrape endplate tissue. Sharp edges 336 may also be used to cut tissue when the jaws perform a scissoring action. The edges 336 may be beveled, scalloped or serrated. Second jaw 328 also may have a concaved inner surface 334 for scoping tissue. First 326 may also include sharp edges 337 that may be used to scrape endplate tissue. Furthermore, jaw 326 and jaw 328 may include respective blunt ends 341 and 343 which assist in preventing damage to surrounding tissue, such as annulus tissue when the tool is inserted and manipulated during scraping. Turning back to FIG. 46, tissue disruption tool may be associated with a housing or handle 338 that includes an actuation member 340, such a rotatable knob, that is actuated to move the second shaft 318 relative to the first shaft 312.

FIGS. 53-60 illustrate tissue disruption tools that include an articulating tissue disruptor associated with the distal end of the tool. The tool includes a first shaft 342 having a distal end 344 and second shaft 346 having a distal end 348. The tool includes a disruptor pivotally attached to the first shaft 342 at a first joint 350 and pivotally attached to the second shaft 346 at a second joint 352. The shafts 342 and 346 may be linearly moveable relative to one another to move the disruptor from a first configuration relatively in-line with the shafts 342 and 346 to a second configuration wherein the disruptor extends at an angle to the shafts 342 and 346.

Figure 53:
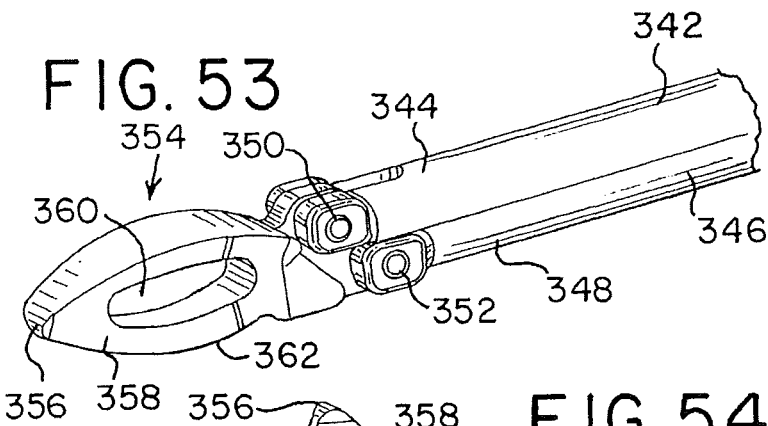
FIGS. 53 and 54 are perspective views of another embodiment of a tissue disruption tool in accordance with the present disclosure.
Figure 54:
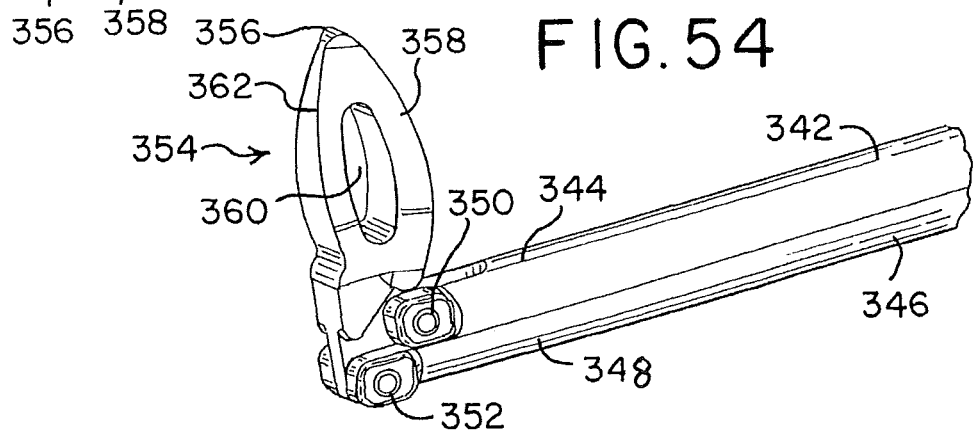

Referring to FIGS. 53 and 54, tissue disruptor 354 has a generally ogive shape that includes a pointed distal end portion 356 which may be suited for puncturing endplates. Additionally, the surfaces 358 on one or both sides of disruptor 354 may be beveled or angled in toward a center opening 360. The outer edges 362 of side surfaces 358 may be sharp or otherwise configured to cut and/or scrape tissue. For example, outer edges 362 may be configured to contact the superior and inferior endplates of the vertebral body. Center opening 360 may collect disrupted tissue for removal for the disc space when the tool is removed. As discussed above, the tissue disruptor 354 is articulated by moving the first and second shafts 342 and 346 relative to one another. For example, as shown in FIG. 54, the tissue disruptor 354 may have an initial generally straight configuration that is generally in-line with shafts 342 and 346. This generally linear configuration may be particularly suited for inserting the tissue disruption tool into the disc space. When the second shaft 346 is moved proximal to the first shaft 342, the tissue disruptor 354 pivots at the first and second joints 350, 352 to thereby result in the tissue disruptor to articulate relative to the shafts. The disruptor may be moved back and forth in the straight, in-line or angled configurations to disrupt tissue.

Figure 55:
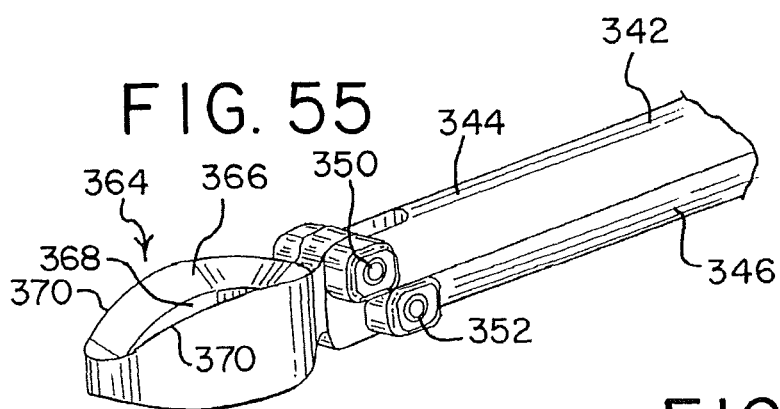
FIGS. 55 and 56 are perspective views of another embodiment of a tissue disruption tool in accordance with the present disclosure.
Figure 56:
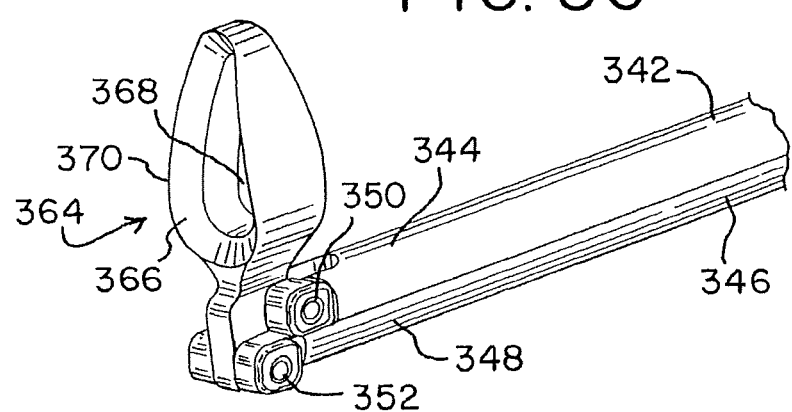

In FIGS. 55 and 56, tissue disruptor 364 has a generally ogive shape, wherein the upper and lower surfaces 366 are beveled or angles inward toward a center opening 368. The outer edges 370 of the upper and lower surfaces 366 may be sharp or otherwise configured to cut and/or scrape tissue, such as endplate tissue.

Figure 57:
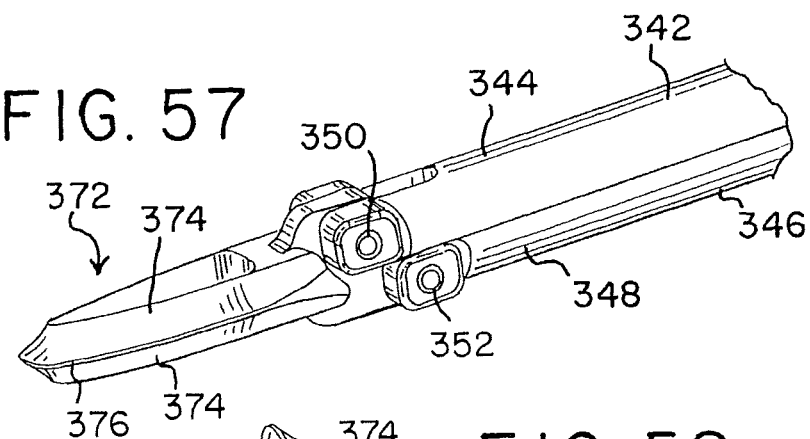
FIGS. 57 and 58 are perspective views of another embodiment of a tissue disruption tool in accordance with the present disclosure.
Figure 58:
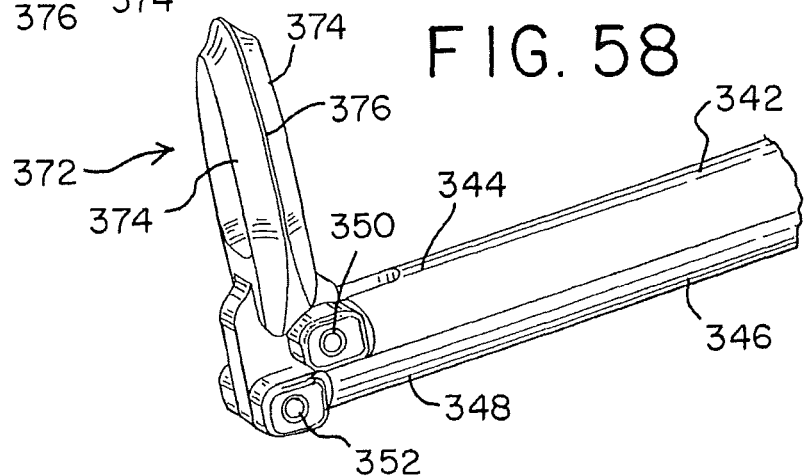

In FIGS. 57 and 58, tissue disruptor 372 has a generally ogive shape, wherein the upper and lower surfaces 374 are beveled or angled outwardly and meet at an edge 376 that may be sharp or otherwise configured to cut and/or scrape tissue, such as endplate tissue.

Figure 59:
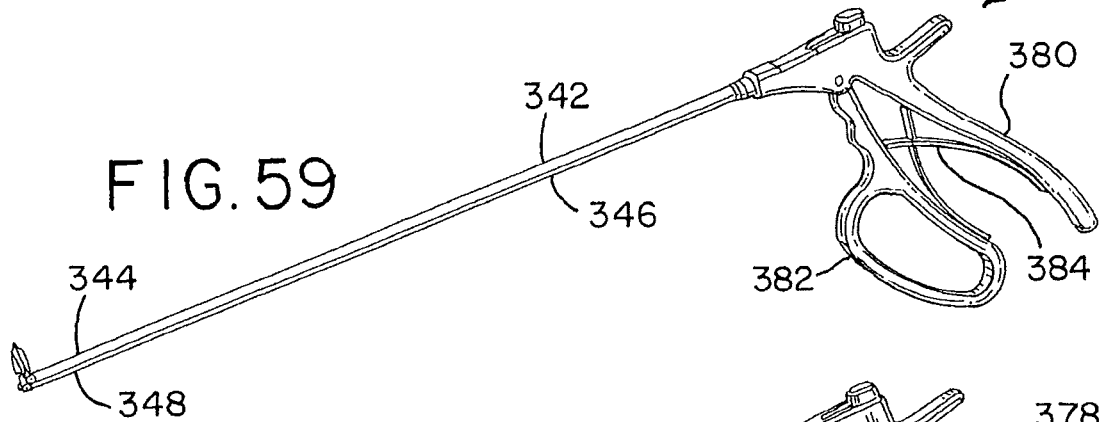
FIGS. 59 and 60 are perspective views of a tissue disruption tool including an actuator for moving the position of the tissue disruptor.
Figure 60:
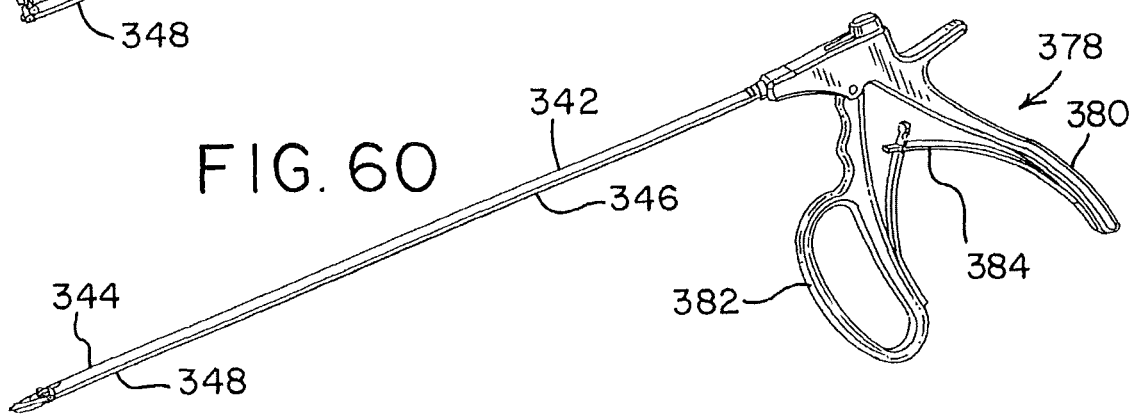

FIGS. 59 and 60 illustrate an embodiment wherein the tissue disruption tool includes an actuator, such as handle 378, which may be used to move the first and second shafts 342 and 346 relative to one another. The handle 378 includes a stationary grip 380 and a pivotal grip 382 pivotally connected to the handle 378. The handle 378 also includes a biasing member 384 that biased the pivotal grip 382 away from the stationary grip 380. When the pivotal grip 382 is moved toward the stationary grip 380, the second shaft 346 moves distally relative to the first shaft 342 to articulate the tissue disruptor.

FIGS. 61 and 62 illustrate another embodiment of tissue disruption tool 400 that includes an articulating tissue disruptor 402. Tissue disruption tool 400 includes a shaft 404 that has a proximal end 406 and distal end 408. The tool is shown inserted into a disc space through an access cannula 410. The disruptor 402 is pivotally attached to the distal end portion 408 at joint 409. Disruptor 402 includes upper and/or lower sharp edges 403 that are configured to disrupt tissue. Such edges 403 may be particularly suited to disrupt endplate tissue. Disruptor 402 also may include a blunt end 405 that protects tissue as the tool is inserted and disrupts tissue. An actuator, such a handle 412, is located at the proximal end portion 406 of shaft 404. The handle 412 includes a stationary grip 414 and a pivotal grip 416 pivotally connected to the handle 412. When the pivotal grip 416 is moved toward the stationary grip 414, the disruptor 402 moves from a first configuration generally in-line with the shaft 404 to a second angled configuration relative to shaft 404. The actuator may be used to move disruptor 402 back and forth and/or disruptor 402 may be pushed back and forth by the shafts.

FIGS. 63-69 illustrate another embodiment of a tissue disruption tool 420, which includes articulating jaws associated with the distal ends of the shafts of the tool. The jaws are moveable between a first, generally linear configuration in which the jaws are generally in-line with the shafts of the tool to a second condition in which the jaws extend at an angle to the shafts. The jaws may be placed in the first, generally in-line configuration to insert the jaws into the treatment site. In the treatment site, the jaws may be moved to the second, angled configuration to reach tissue contralateral to the access site.

Figure 66:
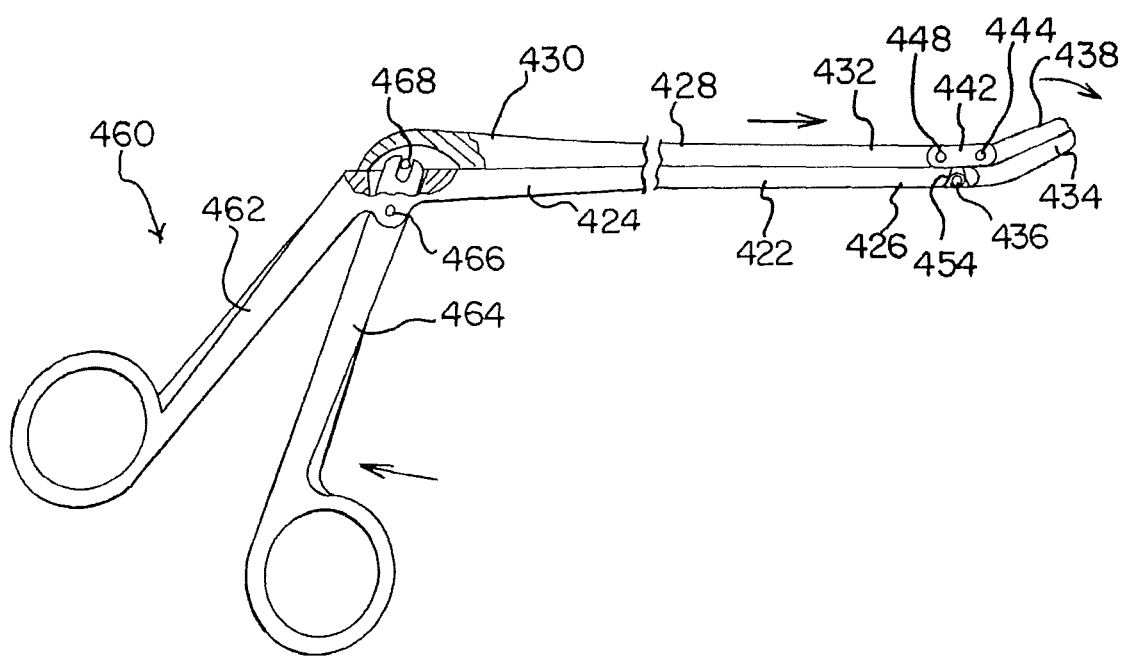
FIG. 66 is a side view of the tissue disruption tool of FIG. 63 shown with the jaws in a closed position and the distal end portion in a substantially straight configuration.
Figure 67A:
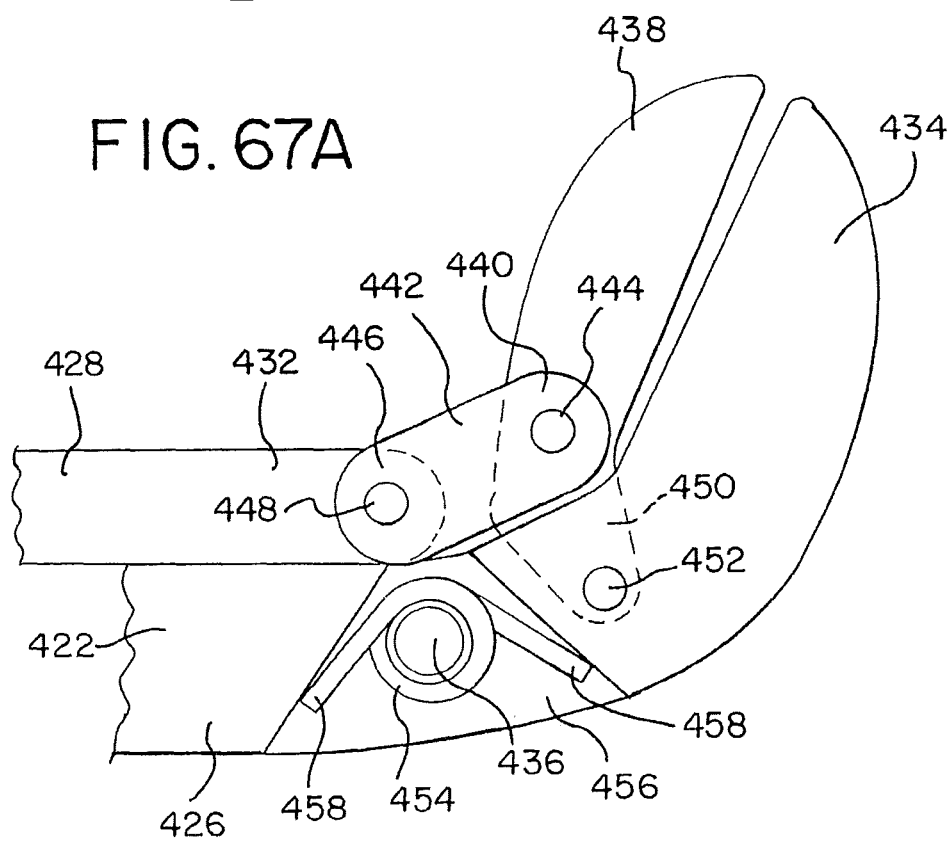
FIGS. 67A-67C are partial side views of one embodiment of the jaws of the tissue disruption tool of FIG. 63.
Figure 67B:
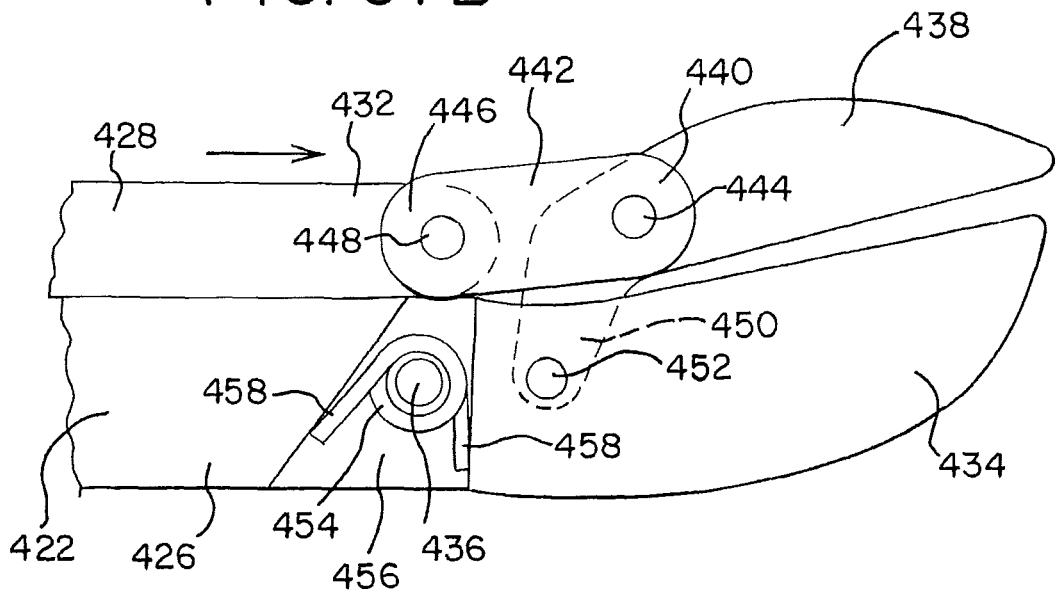

Turning to FIGS. 63-66, disruption tool 420 includes a first elongated shaft 422 having a proximal end portion 424 and a distal end portion 426. The tool 420 also includes a second elongated shaft 428 that has a proximal end portion 430 and a distal end portion 432. Referring to FIGS. 67A-67B, tool 420 includes a first jaw 434 pivotally attached to the distal end 426 of the first shaft 422 at joint 436. The tool 420 also included a second jaw 438 opposed to first jaw 434. The second jaw 438 is pivotally attached to the distal end 440 of a link 442 at joint 444. The proximal end 446 of the link 442 is pivotally attached to the distal end 432 of the second shaft 428 at joint 448. The proximal end 450 of second jaw 438 is pivotally attached to the first jaw at joint 452. The first jaw includes a biasing member 454. In the illustrated embodiment, tool 420 includes a torsion spring that is centered about joint 436 and resides in a cavity 456 between first jaw 434 and distal end portion 426 of shaft 422. The terminal ends 458 of the torsion spring contact the first jaw 434 and distal end portion 426 to bias the jaw to the angle configuration.

Turning back to FIGS. 63-66, tool 420 includes a actuator, such as handle 460 which includes a stationary grip 462 connected to the proximal end portion 424 of the first shaft 422. The handle 460 also includes a pivotal grip 464 which is pivotally attached to handle 460 at joint 466 and pivotally attached to the proximal end portion 430 of second shaft 428 at joint 468.

Figure 67C:
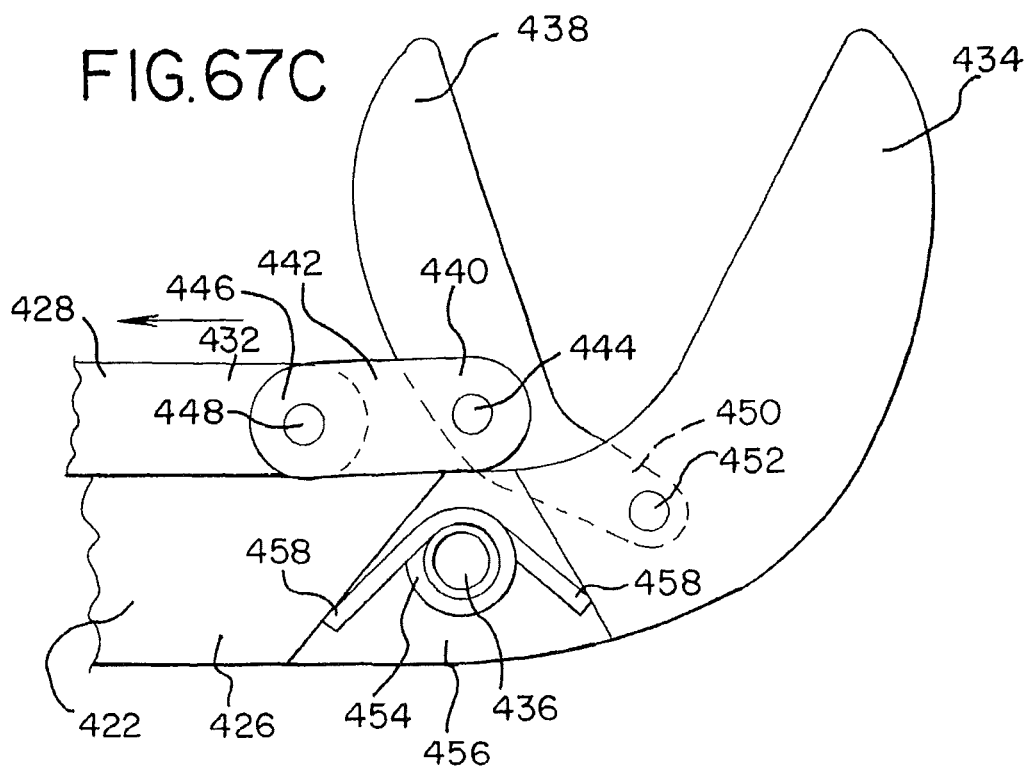

FIGS. 65 and 67A show jaws 434 and 438 in their initial configuration, biased to the angled configuration wherein the jaws 434 and 438 extend at an angle to shafts 422 and 428. Turning to FIGS. 66 and 67B, when the pivotal grip 464 is moved toward stationary grip 462, the second shaft 428 moves distally relative first shaft 422, moving jaws 434 and 438 into an in-line or generally straight configuration. This generally in-line configuration may be the first configuration the jaws 434 and 438 are placed into for insertion into a treatment site. The jaws 434 and 438 being in-line with the shafts 422 and 428 make it easier to insert the tool through an access cannula. Once the jaws are in the treatment site, the pivotal grip 464 may be moved back into the position shown in FIGS. 65 and 67A, thereby moving the second shaft 428 proximally and placing the jaws back into an angled configuration. Turning to FIGS. 64 and 67C, the pivotal grip 464 may be moved further away from stationary grip 462 to move shaft 428 further distally relative to shaft 422, thereby opening jaws 434 and 438. The jaws 434 and 438 may then be place to grasp or cut tissue in a scissor action and moved back into the closed position shown in FIGS. 65 and 67A. The jaws 434 and 438 may then be placed back into the in-line configuration shown in FIGS. 66 and 67B to remove the jaws 434 and 438 and tissue therebetween from the treatment site.

FIGS. 68 and 69 illustrate an embodiment wherein the tool includes a flat or leaf spring 470 attached to shaft 422 and jaw 434 to bias the jaws 434 and 438 to the angled configuration.

Figure 70:
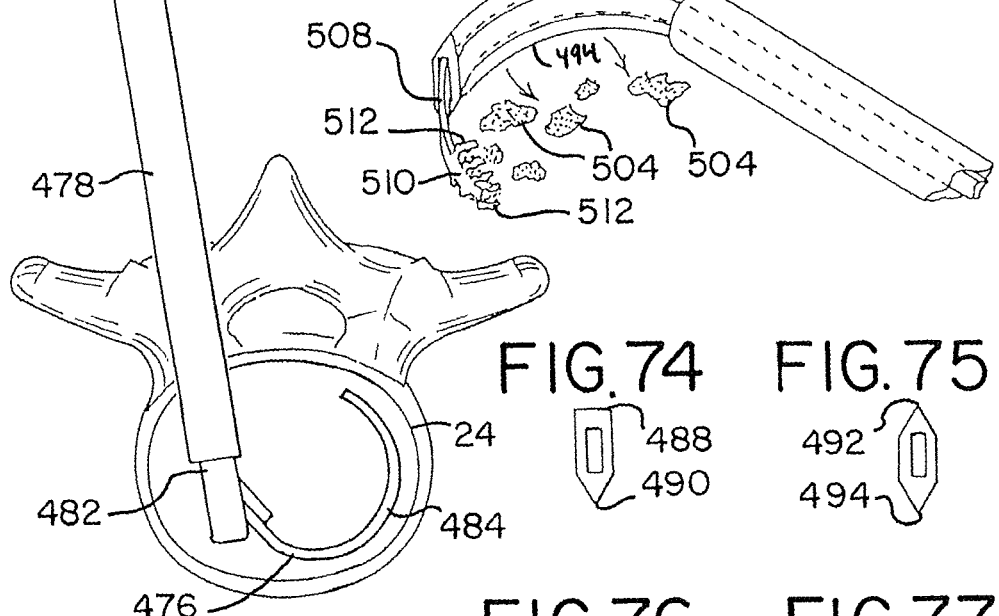
FIG. 70 is a side view of another embodiment of a tissue disruption tool in accordance with the present disclosure.

FIGS. 70-77 illustrate further embodiments of tissue disruption tools of the present disclosure. Referring to FIG. 70, tissue disruption tool 474 may include an elongated member 476 that may be inserted into a disc space 24 through a cannula 478. Tool 474 may include a housing 479 that has an actuator 480 associated therewith to advance and retract the elongated member 476 into our out of the distal end 482 of the cannula 478. The actuator may be of a similar construct to that of tool 240 of FIG. 29. At least the distal end portion 484 of the elongated member 476 is made from a shape memory material that has an initial curved configuration and is constrained by the cannula into a generally straight configuration for deployment into the treatment site. As the distal end portion 484 of the elongated member 476 exits the cannula 478 it returns to it curved configuration. In the illustrated embodiment, the curved configuration is a generally circular configuration, such as circle, oval or ellipse, that extends contralateral to reach tissue contralateral to the access site. As will be described in more detail below, the elongated member may have edges or other features that are conducive for disrupting tissue.

Figure 71:
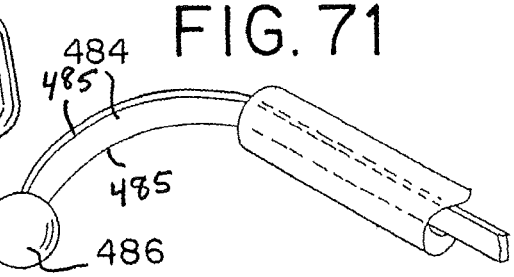
FIG. 71 is a perspective view of another embodiment of a tissue disruption tool in accordance with the present disclosure.

Referring to FIG. 71, the distal end portion 484 of elongated member 476 may have a ball 486 associated with the distal end portion 484. The ball tip 486 may be atraumatic and reduce the risk of the distal end portion from piercing or cutting adjacent or surrounding tissue. The upper and/or lower edges 485 may be sharpened or otherwise configured to disrupt tissue when inserted into the disc space. The ball tip 486 may follow along the annulus without piercing or cutting it.

Figure 72:
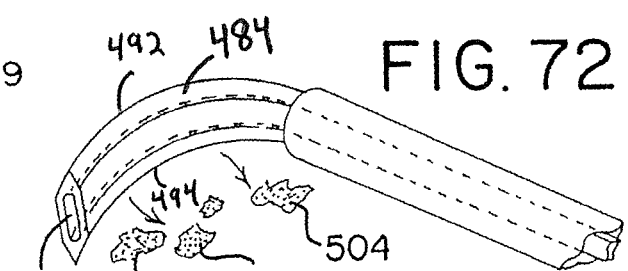
FIG. 72 is a perspective view of another embodiment of a tissue disruption tool in accordance with the present disclosure.
Figure 73:
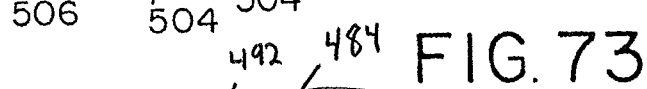
FIG. 73 is a perspective view of another embodiment of a tissue disruption tool in accordance with the present disclosure.
Figures 74, 75:
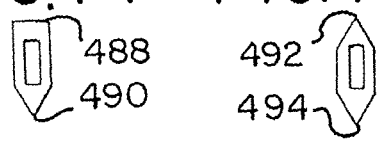
FIGS. 74-77 are cross-sectional views of exemplary profiles of the tissue disruption tools of FIGS. 72 and 73.
Figures 76, 77:

Referring to FIGS. 72 and 73, the distal end portion 484 of elongated member 476 may have a double diamond profile or cross-section in which the upper and lower edges 492, 494 are sharp or otherwise configured to disrupt tissue. The upper and lower edges may be particularly configured to scrape endplate tissue. The upper and lower edges of distal portion 484 may have other configurations as well, such as those showing in FIGS. 74-77. For example, referring to FIG. 74, the upper cutting edge 488 may be smooth while the lower cutting edge may come to a pointed edge 490. Referring to FIG. 75, both the upper cutting edge 492 and the lower cutting edge 494 may come to a pointed edge. Referring to FIG. 76, the upper edge 496 and the lower edge 498 may be rounded. Referring to FIG. 77, the upper edge 500 and lower edge 502 may be scalloped in one direction or the other.

Referring back to FIGS. 72 and 73, when the distal end portion 482 of elongated member 476 is inserted and extended through tissue, it may disrupt the tissue into pieces 504. The elongate member 476 may include a lumen 506 for passage of another tissue disruption tool therethrough, such as tissue grasper 508. The tissue grasper 508 may include a distal end portion 510 that includes bristles or tines 512 for capturing or grasping tissue 504 for removal from the treatment site.

FIG. 78 illustrates another embodiment of tissue disruption tool 514 that includes a delivery cannula 516 and an elongated member 518 that may be inserted into the treatment site through the delivery cannula. The distal end portion 520 of the elongated member 518 is generally looped shaped and may be about 10 mm in diameter. Also, the height of the loop may be such that the top surface and the bottom surface 526, 528 of the loop contact the upper and lower endplates simultaneously. The looped distal end portion 520 may be passed through the cannula 516 in a compact or linear configuration and upon exiting the cannula 516, the distal end portion 520 opens into the looped shape shown. The looped shape distal end portion 520 may then be drawn back into the cannula 516 for removal from the treatment site. The looped shaped distal end portion 520 may have any suitable profile for disrupting tissue. Referring to FIG. 79, for example, the profile or cross-section of the distal end portion 520 may be generally square. Referring to FIG. 80, the profile or cross-section of the distal end portion 520 may be trapezoidal wherein the inner and outer edges 522 and 524 are beveled. As illustrated in FIGS. 81-83, the upper 526 and lower surfaces 528 may be flat (FIG. 81), serrated (FIG. 82) or scalloped (FIG. 83). The distal end portion may also include any of the profiles shown in FIGS. 74-77.

FIG. 84 illustrated another embodiment of a tissue disruption tool 529 that includes an elongated member 530 that is inserted through a cannula 532. The elongated member includes a distal end portion 534 that includes at least two arms 536 and 538 that are closely adjacent to each other for passage through the cannula and then extend away from each other when they exit the cannula. FIG. 87 also shows an elongated member 540 which includes a distal end portion 542 include two arms 544 and 546 that may come together for passage through a cannula and then separate outside of the cannula. In this embodiment one or both of the arms may have pointed distal ends 548. The arms of these embodiments may include any of the profiles shown in FIGS. 74-77 and 79-83. Additionally, the arms may be configured to cut and scrape endplate tissue.

FIGS. 85 and 86 show another embodiment of a tissue disruption tool 550 of the present disclosure. Tool 550 includes an elongated member 552 that may be inserted through a cannula 554 in a straight configuration wherein at least the distal end portion 556 of the elongated 552 forms a curved configuration when it is advanced out of the cannula. In this embodiment, the distal end portion includes a spoon-like scallop 558 for disrupting tissue extending along the inner curved surface of the distal end portion 556. The upper and lower edges 557, 558 may be configured to disrupt endplate tissue.

FIG. 88 illustrates another embodiment of a tissue disruption tool 560 of the present disclose. Tool 560 includes an elongated member 562 that has a slight curved distal end portion 564 having a pointed tip 566. The elongated member 562 may be passed through cannula 568 for insertion into the disc space. When inserted, the slight curve may be in the distal end portion 564 may be orientated so that the pointed tip contacts the upper or lower endplate.

Any of the disruption surfaces and/or edges of the tissue disruptors disclosed herein may have any suitable edge or surface for disrupting tissue. The surface or edge may be sharp, beveled, serrated, scalloped or the like.

Although the present disclosure is described in light of the illustrated embodiments, it is understood that this for the purposes illustration and not limitation. Other applications, modifications or use of the support or distraction device may be made without departing for the scope of this invention, as set forth in the claims now or hereafter filed.

What is claimed is:

1. A method for disrupting tissue in the intervertebral disc space, comprising:
    forming a barrier in the intervertebral disc space wherein the barrier at least partially defines a perimeter of a working region within the disc space, wherein forming of the barrier comprises inserting a barrier into the intervertebral disc space in a substantially linear configuration, wherein the configuration of the barrier changes to a generally arcuate configuration; and
    disrupting tissue on only one side of the barrier and within the working region up to a distalmost tip of the barrier, without disrupting tissue beyond the distalmost tip of the barrier, wherein disrupting tissue within the perimeter comprises cutting, scraping, puncturing, brushing, tearing and/or extracting tissue.

2. The method of claim 1 wherein the tissue within the perimeter comprises nucleus pulposus tissue, vertebral body end plate tissue and/or annulus fibrosus tissue.

3. The method of claim 1 wherein the generally arcuate configuration comprises a partial generally circular shape.

4. The method of claim 1 wherein the generally arcuate configuration extends between about 270 degrees and about 355 degrees.

5. The method of claim 1 wherein the barrier substantially completely surrounds tissue to be disrupted.

6. The method of claim 1 wherein disrupting tissue within the working region comprises inserting a tissue disruption tool within the perimeter.

7. The method of claim 1 wherein forming the barrier within the disc space isolates tissue to be disrupted from other tissue within the disc space.

8. The method of claim 6, wherein the tissue disruption tool is advanced along at least a portion of the barrier to disrupt tissue within the working region.

9. The method of claim 6, further comprising advancing a delivery cannula into the intervertebral disc space, the delivery cannula having the barrier and the tissue disruption tool at least partially positioned therein, with the barrier in a substantially linear configuration.

10. The method of claim 6, wherein the perimeter defined by the barrier is generally circular and includes an open access region configured for passage of the tissue disruption tool therethrough and into the working region.

11. The method of claim 6, wherein the tissue disruption tool includes a distal end portion having a tissue disruptor associated therewith.

12. The method of claim 11, wherein the tissue disruptor comprises one or more of sharp edges, jaws, and bristles.

13. The method of claim 11, wherein the tissue disruption tool comprises at least one shaft, and the distal end portion of the tissue disruption tool is connected to the shaft by a joint that allows the distal end portion of the tissue disruption tool to move relative to the shaft.

14. The method of claim 1, wherein the barrier comprises a ribbon of material.

15. The method of claim 1, wherein the barrier is formed of a shape memory material.

16. A method for disrupting tissue in an intervertebral disc space, comprising:
forming a barrier in the intervertebral disc space wherein the barrier at least partially defines a perimeter of a working region within the disc space; and
disrupting tissue on only one side of the barrier and within the working region up to a distalmost tip of the barrier, without disrupting tissue beyond the distalmost tip of the barrier, wherein disrupting tissue within the working region comprises inserting a tissue disruption tool within the perimeter; and
advancing a delivery cannula into the intervertebral disc space, the delivery cannula having the barrier and the tissue disruption tool at least partially positioned therein, with the barrier in a substantially linear configuration, wherein the delivery cannula includes first and second lumens, with the barrier at least partially positioned within one of the first and second lumens and the tissue disruption tool at least partially positioned within the other one of the first and second lumens.

17. The method of claim 16 wherein the tissue disruption tool is advanced along at least a portion of the barrier to disrupt tissue within the working region.

18. The method of claim 16 wherein the perimeter defined by the barrier is generally circular and includes an open access region configured for passage of the tissue disruption tool therethrough and into the working region.

19. The method of claim 16 wherein the tissue disruption tool includes a distal end portion having a tissue disruptor associated therewith, wherein the tissue disruptor comprises one or more of sharp edges, jaws, and bristles.

20. A method for disrupting tissue in the intervertebral disc space, comprising:
advancing a delivery cannula into an intervertebral disc space, the delivery cannula having a barrier member and a tissue disruption tool at least partially positioned therein, with the barrier member in a first configuration;
advancing at least a portion of the barrier member out of the delivery cannula and into the intervertebral disc space in a second configuration to at least partially define a perimeter of a working region within the intervertebral disc space; and
advancing at least a portion of the tissue disruption tool out of the delivery cannula and along said at least a portion of the barrier member into the working region to disrupt tissue on only one side of the barrier member, within the working region, wherein the barrier member substantially completely surrounds tissue to be disrupted.

21. The method of claim 20 wherein the first configuration comprises a substantially linear configuration and the second configuration comprises a generally arcuate configuration.

22. The method of claim 20 wherein advancing at least a portion of the tissue disruption tool comprises cutting, scraping, puncturing, brushing, tearing and/or extracting tissue.

23. The method of claim 20 wherein the barrier is formed of a shape memory material.

24. A method for disrupting tissue in the intervertebral disc space, comprising:
advancing a delivery cannula into an intervertebral disc space, the delivery cannula having first and second lumens, with a barrier member at least partially positioned within one of the first and second lumens in a first configuration and a tissue disruption tool at least partially positioned within the other one of the first and second lumens;
advancing at least a portion of the barrier member out of the delivery cannula and into the intervertebral disc space in a second configuration to at least partially define a perimeter of a working region within the intervertebral disc space; and
advancing at least a portion of the tissue disruption tool out of the delivery cannula and along said at least a portion of the barrier member into the working region to disrupt tissue on only one side of the barrier member, within the working region.

25. The method of claim 24 wherein the first configuration comprises a substantially linear configuration and the second configuration comprises a generally arcuate configuration.

26. The method of claim 25 wherein the generally arcuate configuration extends between about 270 degrees and about 355 degrees.

27. The method of claim 24 wherein the perimeter defined by the barrier is generally circular and includes an open access region configured for passage of the tissue disruption tool therethrough and into the working region.

28. The method of claim 24 wherein the tissue disruptor comprises one or more of sharp edges, jaws, and bristles.

29. The method of claim 24 wherein the tissue disruption tool comprises at least one shaft, and the tissue disruption tool is connected to the shaft by a joint that allows the tissue disruption tool to move relative to the shaft.

30. The method of claim 24 wherein the barrier comprises a shape memory material.

\* \* \* \* \*